(12) United States Patent
Oliver

(10) Patent No.: US 8,715,933 B2
(45) Date of Patent: May 6, 2014

(54) ASSAY METHODS USING NICKING ENDONUCLEASES

(75) Inventor: John S. Oliver, Bristol, RI (US)

(73) Assignee: Nabsys, Inc., Providence, RI (US)

( * ) Notice: Subject to any disclaimer, the term of this patent is extended or adjusted under 35 U.S.C. 154(b) by 482 days.

(21) Appl. No.: 12/891,343

(22) Filed: Sep. 27, 2010

(65) Prior Publication Data
US 2012/0074925 A1    Mar. 29, 2012

(51) Int. Cl.
*C12Q 1/68* (2006.01)

(52) U.S. Cl.
USPC ............ 435/6.11; 435/6.1; 435/7.1; 435/91.1

(58) Field of Classification Search
None
See application file for complete search history.

(56) References Cited

U.S. PATENT DOCUMENTS

| | | |
|---|---|---|
| 3,699,437 A | 10/1972 | Ur |
| H201 H | 1/1987 | Yager |
| 4,810,650 A | 3/1989 | Kell et al. |
| 4,874,499 A | 10/1989 | Smith et al. |
| 5,194,133 A | 3/1993 | Clark et al. |
| 5,202,231 A | 4/1993 | Drmanac et al. |
| 5,314,829 A | 5/1994 | Coles |
| 5,405,519 A | 4/1995 | Schwartz |
| 5,427,663 A | 6/1995 | Austin et al. |
| 5,455,166 A | 10/1995 | Walker |
| 5,539,082 A | 7/1996 | Nielsen et al. |
| 5,560,811 A | 10/1996 | Briggs et al. |
| 5,599,664 A | 2/1997 | Schwartz |
| 5,650,305 A | 7/1997 | Hui et al. |
| 5,681,947 A | 10/1997 | Bergstrom et al. |
| 5,683,881 A | 11/1997 | Skiena |
| 5,720,928 A | 2/1998 | Schwartz |
| 5,744,366 A | 4/1998 | Kricka et al. |
| 5,773,571 A | 6/1998 | Nielsen et al. |
| 5,795,782 A | 8/1998 | Church et al. |
| 5,824,477 A | 10/1998 | Stanley |
| 5,837,115 A | 11/1998 | Austin et al. |
| 5,908,745 A | 6/1999 | Mirzabekov et al. |
| 5,972,619 A | 10/1999 | Drmanac et al. |
| 6,015,714 A | 1/2000 | Baldarelli et al. |
| 6,020,599 A | 2/2000 | Yeo |
| 6,025,891 A | 2/2000 | Kim |
| 6,084,648 A | 7/2000 | Yeo |
| 6,100,949 A | 8/2000 | Kim |
| 6,108,666 A | 8/2000 | Floratos et al. |
| 6,128,051 A | 10/2000 | Kim et al. |
| 6,147,198 A | 11/2000 | Schwartz |
| 6,150,089 A | 11/2000 | Schwartz |
| 6,174,671 B1 | 1/2001 | Anantharaman et al. |
| 6,182,733 B1 | 2/2001 | McReynolds |
| 6,210,891 B1 | 4/2001 | Nyren et al. |
| 6,210,896 B1 | 4/2001 | Chan |
| 6,258,568 B1 | 7/2001 | Nyren |
| 6,263,286 B1 | 7/2001 | Gilmanshin et al. |
| 6,267,872 B1 | 7/2001 | Akeson et al. |
| 6,274,320 B1 | 8/2001 | Rothberg et al. |
| 6,294,136 B1 | 9/2001 | Schwartz |
| 6,303,288 B1 | 10/2001 | Furcht et al. |
| 6,304,318 B1 | 10/2001 | Matsumoto |
| 6,340,567 B1 | 1/2002 | Schwartz et al. |
| 6,355,420 B1 | 3/2002 | Chan |
| 6,362,002 B1 | 3/2002 | Denison et al. |
| 6,392,719 B2 | 5/2002 | Kim |
| 6,400,425 B1 | 6/2002 | Kim et al. |
| 6,403,311 B1 | 6/2002 | Chan |
| 6,410,243 B1 | 6/2002 | Wyrick et al. |
| 6,413,792 B1 | 7/2002 | Sauer et al. |
| 6,428,959 B1 | 8/2002 | Deamer |
| 6,448,012 B1 | 9/2002 | Schwartz |
| 6,464,842 B1 | 10/2002 | Golovchenko et al. |
| 6,503,409 B1 | 1/2003 | Fleming |
| 6,509,158 B1 | 1/2003 | Schwartz |
| 6,537,755 B1 | 3/2003 | Drmanac |
| 6,537,765 B2 | 3/2003 | Stricker-Kongra et al. |
| 6,610,256 B2 | 8/2003 | Schwartz |
| 6,616,895 B2 | 9/2003 | Dugas et al. |
| 6,617,113 B2 | 9/2003 | Deamer |
| 6,627,067 B1 | 9/2003 | Branton et al. |
| 6,672,067 B2 | 1/2004 | Farmer et al. |
| 6,673,615 B2 | 1/2004 | Denison et al. |
| 6,685,841 B2 | 2/2004 | Lopez et al. |
| 6,689,563 B2 | 2/2004 | Preparata et al. |
| 6,696,022 B1 | 2/2004 | Chan et al. |
| 6,713,263 B2 | 3/2004 | Schwartz |

(Continued)

FOREIGN PATENT DOCUMENTS

DE    19936302 A1    2/2001
EP    0958495 B1    11/1999

(Continued)

OTHER PUBLICATIONS

Anderson, P. et al., "Nkx3.1 and Myc crossregulate shared target genes in mouse and human prostate tumorigenesis," J. Clinical Investigation, May 2012, pp. 1907-1919, vol. 122, http://www.jci.org.

Arrowsmith, C. et al., "Epigenetic protein families: a new frontier for drug discovery," Nature Reviews: Drug Discovery, May 2012, pp. 384-400, vol. 11, Macmillan Publishers Limited.

Austin, Robert, "The art of sucking spaghetti", Nature Publishing Group, Nature Materials, vol. 2, pp. 567-568, Sep. 2003.

Bourdoncle, A., et al., "Quaruplex-Based Molecular Beacons as Tunable DNA Probes", J. Am. Chem. Soc., vol. 128, No. 34, pp. 11094-11105, 2006.

Drmanac, R., et al. (2002) "Sequencing by Hybridization (SBH): Advantages, Achievements, and Opportunities," Advances in Biochemical Engineering/Biotechnology, vol. 77: 75-101.

(Continued)

*Primary Examiner* — James Martinell
(74) *Attorney, Agent, or Firm* — Goodwin Procter LLP

(57) ABSTRACT

Assay methods and apparatus for the analysis of biopolymers are disclosed. The assays employ nicking endonucleases to enable the generation of flaps on target biomolecules which are detected in nanopore or fluidic channel devices. Identification of flap locations enables a map of the target biomolecule to be derived.

36 Claims, 18 Drawing Sheets

(56) References Cited

U.S. PATENT DOCUMENTS

| | | |
|---|---|---|
| 6,746,594 B2 | 6/2004 | Akeson et al. |
| 6,762,059 B2 | 7/2004 | Chan et al. |
| 6,772,070 B2 | 8/2004 | Gilmanshin et al. |
| 6,790,671 B1 | 9/2004 | Austin et al. |
| 6,818,395 B1 | 11/2004 | Quake et al. |
| 6,905,586 B2 | 6/2005 | Lee et al. |
| 6,911,345 B2 | 6/2005 | Quake et al. |
| 6,919,002 B2 | 7/2005 | Chopra |
| 6,927,065 B2 | 8/2005 | Chan et al. |
| 6,936,433 B2 | 8/2005 | Akeson et al. |
| 7,001,792 B2 | 2/2006 | Sauer et al. |
| 7,005,264 B2 | 2/2006 | Su et al. |
| 7,034,143 B1 | 4/2006 | Preparata et al. |
| 7,071,324 B2 | 7/2006 | Preparata et al. |
| 7,118,657 B2 | 10/2006 | Golovchenko et al. |
| 7,170,050 B2 | 1/2007 | Turner et al. |
| 7,176,007 B2 | 2/2007 | Cox et al. |
| 7,189,503 B2 | 3/2007 | Akeson et al. |
| 7,211,414 B2 | 5/2007 | Hardin et |
| 7,217,562 B2 | 5/2007 | Cao et al. |
| 7,238,485 B2 | 7/2007 | Akeson et al. |
| 7,248,771 B2 | 7/2007 | Schmidt et al. |
| 7,250,115 B2 | 7/2007 | Barth |
| 7,262,859 B2 | 8/2007 | Larson et al. |
| 7,279,337 B2 | 10/2007 | Zhu |
| 7,282,130 B2 | 10/2007 | Flory |
| 7,282,330 B2 | 10/2007 | Zhao et al. |
| 7,297,518 B2 | 11/2007 | Quake et al. |
| 7,302,146 B2 | 11/2007 | Turner et al. |
| 7,315,019 B2 | 1/2008 | Turner et al. |
| 7,329,492 B2 | 2/2008 | Hardin et al. |
| 7,351,538 B2 | 4/2008 | Fuchs et al. |
| 7,355,216 B2 | 4/2008 | Yang et al. |
| 7,371,520 B2 | 5/2008 | Zhao et al. |
| 7,402,422 B2 | 7/2008 | Fuchs et al. |
| 7,462,449 B2 | 12/2008 | Quake |
| 7,476,503 B2 | 1/2009 | Turner et al. |
| 7,476,504 B2 | 1/2009 | Turner |
| 7,501,245 B2 | 3/2009 | Quake et al. |
| 7,595,160 B2 | 9/2009 | White et al. |
| 7,678,562 B2 | 3/2010 | Ling |
| 8,232,055 B2 | 7/2012 | Bruhn et al. |
| 8,246,799 B2 | 8/2012 | Oliver et al. |
| 8,278,050 B2 | 10/2012 | Bailey et al. |
| 8,628,919 B2 | 1/2014 | Xiao et al. |
| 2001/0004728 A1 | 6/2001 | Preparata et al. |
| 2002/0028458 A1 | 3/2002 | Lexow |
| 2002/0058279 A1 | 5/2002 | Fritsch et al. |
| 2002/0127855 A1 | 9/2002 | Sauer et al. |
| 2002/0137089 A1 | 9/2002 | Deamer |
| 2003/0003609 A1 | 1/2003 | Sauer et al. |
| 2003/0064095 A1 | 4/2003 | Martin et al. |
| 2003/0064382 A1 | 4/2003 | Preparata et al. |
| 2003/0080042 A1 | 5/2003 | Barth et al. |
| 2003/0104428 A1 | 6/2003 | Branton et al. |
| 2003/0143614 A1 | 7/2003 | Drmanac |
| 2003/0186256 A1 | 10/2003 | Fischer |
| 2003/0207326 A1 | 11/2003 | Su et al. |
| 2003/0211502 A1 | 11/2003 | Sauer et al. |
| 2003/0232346 A1 | 12/2003 | Su |
| 2004/0137734 A1 | 7/2004 | Chou et al. |
| 2004/0146430 A1 | 7/2004 | Dugas |
| 2004/0197843 A1 | 10/2004 | Chou et al. |
| 2005/0019784 A1 | 1/2005 | Su et al. |
| 2005/0127035 A1 | 6/2005 | Ling |
| 2006/0019247 A1 | 1/2006 | Su et al. |
| 2006/0063171 A1 | 3/2006 | Akeson et al. |
| 2006/0154399 A1 | 7/2006 | Sauer et al. |
| 2006/0269483 A1 | 11/2006 | Austin et al. |
| 2006/0287833 A1 | 12/2006 | Yakhini |
| 2007/0020772 A1 | 1/2007 | Cao et al. |
| 2007/0039920 A1 | 2/2007 | Kutchoukov et al. |
| 2007/0042366 A1 | 2/2007 | Ling |
| 2007/0080511 A1 | 4/2007 | Campbell |
| 2007/0084163 A1 | 4/2007 | Lai |
| 2007/0084702 A1 | 4/2007 | Lin et al. |
| 2007/0138132 A1 | 6/2007 | Barth |
| 2007/0178240 A1 | 8/2007 | Yamazaki et al. |
| 2007/0190542 A1 | 8/2007 | Ling et al. |
| 2007/0218471 A1 | 9/2007 | Kim et al. |
| 2007/0231795 A1 | 10/2007 | Su |
| 2007/0238112 A1 | 10/2007 | Sohn et al. |
| 2008/0041733 A1 | 2/2008 | Hibbs et al. |
| 2008/0085840 A1 | 4/2008 | Buzby |
| 2008/0096287 A1 | 4/2008 | Barth |
| 2008/0102504 A1 | 5/2008 | Akeson et al. |
| 2008/0119366 A1 | 5/2008 | Sauer et al. |
| 2008/0171316 A1 | 7/2008 | Golovchenko et al. |
| 2008/0187915 A1 | 8/2008 | Polonsky et al. |
| 2008/0234136 A1 | 9/2008 | Drmanac et al. |
| 2008/0242556 A1 | 10/2008 | Cao et al. |
| 2008/0254995 A1 | 10/2008 | Kim et al. |
| 2009/0005252 A1 | 1/2009 | Drmanac et al. |
| 2009/0011943 A1 | 1/2009 | Drmanac et al. |
| 2009/0035777 A1 | 2/2009 | Kokoris et al. |
| 2009/0099786 A1 | 4/2009 | Oliver et al. |
| 2009/0111115 A1 | 4/2009 | Drmanac et al. |
| 2009/0117540 A1* | 5/2009 | Sorge ................................ 435/6 |
| 2009/0136948 A1 | 5/2009 | Han et al. |
| 2009/0176652 A1 | 7/2009 | Dahl et al. |
| 2009/0214392 A1 | 8/2009 | Kameoka et al. |
| 2010/0078325 A1 | 4/2010 | Oliver |
| 2010/0096268 A1 | 4/2010 | Ling et al. |
| 2010/0143960 A1 | 6/2010 | Bazin |
| 2010/0243449 A1 | 9/2010 | Oliver |
| 2010/0297644 A1 | 11/2010 | Kokoris et al. |
| 2012/0074925 A1 | 3/2012 | Oliver |

FOREIGN PATENT DOCUMENTS

| | | |
|---|---|---|
| EP | 1486775 | 12/2004 |
| EP | 1685407 | 8/2006 |
| WO | WO-9004652 | 5/1990 |
| WO | WO-9322678 A2 | 11/1993 |
| WO | WO-9617957 | 6/1996 |
| WO | WO-9835012 | 8/1998 |
| WO | WO-0009757 | 2/2000 |
| WO | WO-0011220 A1 | 3/2000 |
| WO | WO-0020626 A1 | 4/2000 |
| WO | WO-0022171 | 4/2000 |
| WO | WO-0062931 A1 | 10/2000 |
| WO | WO-0118246 | 3/2001 |
| WO | WO-0131063 A1 | 5/2001 |
| WO | WO-0133216 A1 | 5/2001 |
| WO | WO-0137958 | 5/2001 |
| WO | WO-0142782 | 6/2001 |
| WO | WO-0146467 A2 | 6/2001 |
| WO | WO-0207199 | 1/2002 |
| WO | WO-0250534 | 6/2002 |
| WO | WO-03000920 | 1/2003 |
| WO | WO-03010289 | 2/2003 |
| WO | WO-03079416 | 9/2003 |
| WO | WO-03089666 A2 | 10/2003 |
| WO | WO-03106693 | 12/2003 |
| WO | WO-2004035211 | 4/2004 |
| WO | WO-2004085609 | 10/2004 |
| WO | WO-2005017025 | 2/2005 |
| WO | WO-2006020775 | 2/2006 |
| WO | WO-2006028508 | 3/2006 |
| WO | WO-2006052882 | 5/2006 |
| WO | WO-2007106509 | 9/2007 |
| WO | WO-2007111924 | 10/2007 |
| WO | WO-2007127327 | 11/2007 |
| WO | WO-2008021488 | 2/2008 |
| WO | WO-2008039579 | 4/2008 |
| WO | WO-2008042018 | 4/2008 |
| WO | WO-2008046923 | 4/2008 |
| WO | WO-2008049021 | 4/2008 |
| WO | WO-2008069973 | 6/2008 |

(56) References Cited

FOREIGN PATENT DOCUMENTS

| WO | WO-2008079169 | 7/2008 |
|---|---|---|
| WO | WO-2010111605 | 9/2010 |
| WO | WO-2010138136 | 12/2010 |

OTHER PUBLICATIONS

Greer, E. et al., "Histone methylation: a dynamic mark in health, disease and inheritance," Nature Review: Genetics, May 2012, pp. 343-357, vol. 13, Macmillan Publishers Limited.
Hannenhalli S. et al. Comput Appl Biosci (1996) 12 (1): 19-24.
Heyn, H. et al., "DNA methylation profiling in the clinic: applications and challenges," Nature Review: Genetics, Oct. 2012, pp. 679-692, vol. 13, Macmillan Publishers Limited.
International Preliminary Report on Patentability, Application No. PCT/US2010/028848, issuance date Sep. 27, 2011, 8 pages.
International Search Report and Written Opinion dated Feb. 5, 2009, PCT/US08/078432.
International Search Report and Written Opinion dated Oct. 25, 2012, PCT/US12/024708.
Invitation to Pay Additional Fees and, Where Applicable, Protest Fee & Partial International Search dated Feb. 15, 2013, PCT/US2011/053274, 9 pages.
Invitation to Pay Additional Fees and, Where Applicable, Protest Fee & Partial International Search dated Jul. 10, 2012, PCT/US2012/024708, 10 pages.
Langer-Safer, P. et al., "Immunological method for mapping genes on *Drosophila* polytene chromosomes," Proc. Natl. Acad. Sci. USA, Jul. 1982, pp. 4381-4385, vol. 79.
Lennon, Erwan et al., "Evaporative Pumping of Liquid in Nanochannel for Electrical Measurement of a Single Biomolecule in Nanofluidic Format", Proceedings of the 7th IEEE Internation Conference on Nantechnology, Hong Kong, Aug. 2-5, 2007, pp. 562-565.
Park, P., "ChIP-seq: advantages and challenges of a maturing technology," Nature Reviews: Genetics, Oct. 2009, pp. 669-680, vol. 10, Macmillan Publishers Limited.
Pastor, W. et al., "Genome-wide mapping of 5-hydroxymethylcytosine in embryonic stem cells," Nature, May 19, 2011, pp. 394-397, vol. 473, Macmillan Publishers Limited.
Rapley, Ralph, "Enhancing PCR Amplification and Sequencing Using DNA-Binding Proteins", Molecular Biotechnology, vol. 2, pp. 295-298, 1994.
Riccelli, P. V. et al., "Hybridization of single-stranded DNA targets to immobilized complementary DNA probes: comparison of hairpin versus linear capture probes", Oxford University Press, Nucleic Acids Research, vol. 29, No. 4, pp. 996-1004, 2001.
Ross-Innes, C. et al., "Differential oestrogen receptor binding is associated with clinical outcome in breast cancer," Nature, Jan. 2012, pp. 389-394, vol. 481, Macmillan Publishers Limited.
Salpea, P. et al., "Postnatal development- and age-related changes in DNA-methylation patterns in the human genome," Nucleic Acids Research, 2012, pp. 6477-6494, vol. 40, No. 14, Oxford University Press.
Shoaib, M. et al., "PUB-NChIP2-"in vivo biotinylation" approach to study chromatin in proximity to a protein of interest," Genome Research, 2013, pp. 331-340, vol. 23, Cold Spring Harbor Laboratory Press, www.genome.org.
van Steensel, B. et al., "Identification of in vivo DNA targets of chromatin proteins using tethered Dam methyltransfarase," Nature Biotechnology, Apr. 2000, pp. 424-428, vol. 18.
Ben-Dor et al, "On the Complexity of Positional Sequencing by Hybridization", Journal of Computational Biology, vol. 8, No. 4, 2001, pp. 361-371.
Bloom, et al, Applications of Numbered Undirected Graphs, Proceedings of the IEEE, vol. 65, No. 4, Apr. 1977, pp. 562-570.
Branton, Daniel et al, "The potential and challenges of anopore sequencing," Nature Biotechnology, vol. 26, No. 10, Oct. 2008, pp. 1146-1153.
Ghosh, et al, Detection of Double-Stranded DNA: molecular methods and applications for DNA diagnostics Molecular Biosystems (2006) vol. 2, pp. 551-560.

International Preliminary Report on Patentability issuance date Apr. 7, 2010, PCT/US2008/078432.
International Preliminary Report on Patentability, Application No. PCT/US2009/055878, mailed Nov. 29, 2011, 9 pages.
International Preliminary Report on Patentability, issuance of report Mar. 8, 2011, Application No. PCT/US2009/055876.
International Search Report and Written Opinion, PCT/US2011/059933, dated Feb. 4, 2012, Apr. 2, 2012.
Akeson, et al., (1999) "Microsecond time-scale discrimination among polycytidylic acid, polyadenylic acid, and polyuridylic acid as homopolymers or as segments within single RNA molecules," Biophys. J. 77, 3227-3233.
Alberts, B., et al., (1970) "T4 Bacteriophage Gene 32: A Structural Protein in the Replication and Recombination of DNA," Nature 227:1313-1318.
Amit, B., et al., (1974) "Photosensitive Protecting Groups of Amino Sugars and Their Use in Glycoside Synthesis. 2-Nitrobenzyloxycarbonylamino and 6-Nitroveratryloxycarbonylamino Derivatives," J. Org. Chem. 39:192-196.
Arratia, R., et al., (1989) "Poisson Process Approximation for Repeats in One Sequence and Its Application to Sequencing by Hybridization," Dept. of Mathematics, University of Southern California.
Ashkin, (1997) "Optical trapping and manipulation of neutral particles using lasers," Proc. Natl. Acad. Sci. USA, vol. 94, DD. 4853-4860.
Austin, M., et al., (2004) "Fabrication of 5 nm Linewidth and 14 nm Pitch Features by Nanoimprint Lithography," App. Phys. Lett. 84:5299-5301.
Bains, W., et al., (1988) "A Novel Method for Nucleic Acid Sequence Determination," J. Theor. Biol. 135:303-307.
Baliga, R., et al., (2001) "Kinetic Consequences of Covalent Linkage of DNA Binding Polyamides," Biochemistry 40:3-8.
Bennett et al., (2005) "Toward the $1000 Human Genome," Pharmacogenomics 6:373-382.
Bianco, P., et al., (1996) "Interaction of the RecA Protein of *Escherichia coli* with Single-Stranded Oligodeoxyribonucleotides," Nucleic Acids Research vol. 24(24):4933-4939.
Buchmueller, K.L., et al., (2005) "Extending the Language of DNA Molecular Recognition by Polyamides: Unexpected Influence of Imidazole and Pyrrole Arrangement on Binding Affinity and Specificity," J. Am. Chem. Soc. 127:742-750.
Buchmueller, K.L., et. al., (2006) "Physical and Structural Basis for the Strong Interactions of the -ImPy- Central Pairing Motif in the Polyamide f-ImPylm," Biochemistry 45:13551-13565.
Cao, H., et al., (2002) "Fabrication of 10 nm Enclosed Nanofluidic Channels," Applied Physics Letters 81(1): 174-176.
Cao, H., et al., (2002) "Gradient Nanostructures for Interfacing Microfluidics and Nanofluidics," Applied Physics Letters 81:3058-3060.
Chen, C., et al., (1994) "Analogous Organic Synthesis of Small-Compound Libraries: Validation of Combinatorial Chemistry in Small-Molecule Synthesis," J. Am. Chem. Soc. 116:2661-2662.
Chen, P., et al., (2004) "Probing Single DNA Molecule Transport Using Fabricated Nanopores," Nano Letters 4:2293-2298.
Chetverin, A., et al., (1994) "Oligonucleotide Arrays: New Concepts and Possibilities," Bio/Technology 12:1093-1099.
Cox, M., (2007) "Motoring Along with the Bacterial RecA Protein," Nature Reviews—Molecular Cell Biology 9:127-138.
Dervan, P.B. (2001) "Molecular Recognition of DNA by Small Molecules," Bioorg. Med. Chem. 9:2215-2235.
Dervan, P.B., et al., (2003) "Recognition of the DNA minor groove by pyrrole-imidazole polyamides," Curr. Op. Struc. Biol. 13:284-299.
Doss, R.M., et al., (2006) "Programmable Oligomers for Minor Groove DNA Recognition," J. Am. Chem. Soc. 128:9074-9079.
Drmanac, R., et al. (1989) "Sequencing of Megabase Plus DNA by Hybridization: Theory of the Method," Genomics 4:114-128.
Ellervik, U., et al., (2000) "Hybroxybenzamide/Pyrrole Pair Distinguishes T-A from A-T Base Pairs in the Minor Groove of DNA," J. Am. Chem. Soc. 122:9354-9360.
Farkas, Z., et al., (2003) "DNA Uptake Into Nuclei: Numerical and Analytical Results," J. Phys.: Condens. Matter 15:S1767-S1777.

(56) References Cited

OTHER PUBLICATIONS

Fechter, E.J., et al., (2005) "Sequence-specific Fluorescence Detection of DNA by Polyamide-Thiazole Orange Conjugates," J. Am. Chem. Soc. 127:16685-16691.
Floreancig, P.E., et al., (2000) "Recognition of the Minor Groove of DNA by Hairpin Polyamides Containing α-Substituted-β-Amino Acids," J. Am. Chem. Soc. 122:6342-6350.
Fodor, S., et al., (2005) "Light-Directed, Spatially Addressable Parall Chemical Synthesis" Research Article 6 pgs.
Fologea, D., et al., (2005) "Slowing DNA Translocation in a Solid-State Nanopore," Nano Lett. 5(9):1734-7.
Frieze, a., et al., (1999) "Optimal Reconstruction of a Sequence From its Probes," 12 pgs.
Gerland, U., et al., (2004) "Translocation of Structured Polynucleotides Through Nanopores," Phys. Biol. 1:19-26.
Gershow, M., et al., (2007) "Recapturing and Trapping Single Molecules with a Solid-State Nanopore," Nature Nanotech. 2:775-779.
Giehart B., et al., (2008) "Nanopore with transverse nanoelectrodes for electrical characterization and sequencing of DNA" Sensors and Actuators B., Elsevier Sequoia S.A, ScienceDirect,132:2 593-600.
Gracheva, M., et al., (2002) "Simulation of the Electric Response of DNA Translocation through a Semiconductor Nanopore-Capacitor," Nanotechnology 17:622-633.
Guo, L., (2004) "Recent Progress in Nanoimprint Technology and its Application," J. Phys. D: Appl. Phys 37:R123-R141 (Appendices B-D).
Gygi, M.P., et al., (2002) "Use of fluorescent sequence-specific polyamides to discriminate human chromosomes by microscopy and flow cytometry," Nucleic Acids Research 30:2790-2799.
Halby, L., et al., (2005) "Functionalized head-to-head hairpin polyamides: Synthesis, double-stranded DNA-binding activity and affinity," Bioorg. Med. Chem. Lett. 15:3720-3724.
Heller, C., (2001) "Principles of DNA Separation with Capillary Electrophoresis," Electrophoresis 22:629-643.
Heng, J., et al., (2004) "Sizing DNA Using a Nanometer-Diameter Pore," Biophysical Journal 87:2905-2911.
Hudson, B., (1999) "An Experimental Study of SBH with Gapped Probes," 50 pgs.
International Search Report mailed May 4, 2006, PCT/US04/04138, 5 pgs.
International Search Report and Written Opinion dated May 2, 2009, PCTUS2008/078432, 8 pgs.
International Search Report and Written Opinion dated Feb. 10, 2010, PCT/US09/558876, 5 pgs.
International Search Report and Written Opinion dated Mar. 24, 2010 for PCT/US09/055878, 13 pgs.
International Search Report and Written Opinion dated Jun. 29, 2010, PCT/US09/055876, 10 pgs.
International Search Report and Written Opinion dated Sep. 30, 2010, PCT/US2010/028848, 14 pgs.
Invitation to Pay Additional Fees and, Where Applicable, Protest Fee & Partial International Search dated Aug. 19, 2010, PCT/US2010/028848, 7 pgs.
Jonsson, U., et al., (1991) "Real-Time Biospecific Interaction Analysis Using Surface Plasmon Resonance and a Sensor Chip Technology," BioTechniques, 11:620-627.
Ju et al., (2006) "Four-color DNA Sequencing by Synthesis Using Cleavable Fluorescent Nucleotide Reversible Terminators," Proc. Nat. Acad. Sci. USA 103:19635-19640.
Kalaugher, L., (2002) "Diffraction Gradient Lithography Aids Nanofluidics," Nanotechweb.org.
Kanehisa, L., (1984) "Use of Statistical Criteria for Screening Potential Homologies in Nucleic Acid Sequences," Nucleic Acids Research 12:203-213.
Kasianowicz et al., (1996) "Characterization of Individual Polynucleotide Molecules Using a Membrane Channel," Proc. Nat. Acad. Sci. USA 93:13770-13773.
Khrapko, K.R. et al., (1989) "An Oligonucleotide Hybridizatioin Approach to DNA Sequencing," FEBS Lett. 256:118-22.

Kim, C., et al., (1992) "Binding Properties of Replication Protein A from Human and Yeast Cells," Mol. and Cell. Bio. 12(7):3050-3059.
Kuo, et al., (2002) "Hybrid three-dimensional nanofluidic/microfluidic devices using molecular gates," Sensors and Actuators A, 102:223-233.
Langa, (2003) "Self-organized growth of single crystals of nanopores," Applied Physics Letters, AIP, American Institute of Physics, 82(2):278-280.
Li et al., (2001) "Lon-beam sculpting at nanometre length scales," Nature 412,166-169.
Liang, X., et al., (2007) "Single Sub-20 nm wide Centimeter-Long NanoFluidic Channel Fabricated by Novel Nanoimprint Mold Fabrication and Divest Imprinting," Nano Letters 7:3774-3780.
Liang, X., et al., (2008) "Nanogap Detector Inside Nanofluidic Channel for Fast Real Time Label-Free DNA Analysis," Nano Letters 8:1472-76.
Loakes, D., et al., (1994) "5-Nitroindole as an Universal Base Analogue," Nucleic Acids Research 22:4039-4043.
Loakes, D., et al., (1995) "3-Nitropyrrole and 5-Nitroindole as Universal Bases in Primers for DNA Sequencing and PCR," 23:2361-2366.
Lohman, T., et al., (1994) "*Escherichia coli* Single-Stranded DNA-Binding Protein: Multiple DNA-Binding Modes and Cooperatives," Annu. Rev. Biochem. 63:527-70.
Losi, et al., (1999) "Time-Resolved Absorption and Photothermal Measurements with Recombinant Sensory Rhodopsin II from *Natronobacterium pharaonis*," Biophys. J. 77, 3277-3286.
Margulies et al., (2005) "Genome Sequencing in Microfabricated High-Density Picolitre Reactors," Nature 437:376-380.
Marques, M.A., et al., (2004) "Expanding the Repertoire of Heterocycle Ring Pairs for Programmable Minor Groove DNA Recognition," J. Am. Chem. Soc. 126:10339-10349.
McEntee, K., et al., (1981) "Binding of the RecA Protein of *Escherichia coli* to Single- and Double-Stranded DNA." J. Biol. Chem. 256:8835.
Meller, A., et al., (2000) "Rapid Nanopore Discrimination Between Single Polynucleotide Molecules," PNAS 97:1079-1084.
Meller, et al., (2001) "Voltage-driven DNA translocations through a nanopore," Phys. Rev. Lett. 86(15):3435-3438.
Nice, E., et al., (1993) "Mapping of the Antibody- and Receptor-Binding Domains of Granulocyte Colony-Stimulating Factor Using an Optical Biosensor," Journal of Chromatography 646:159-168.
Nichols, R., et al., (1994) "A Universal Nucleoside for Use at Ambiguous Sites in DNA Primers," Letters to Nature 369:492-493.
Novopashina, D.S., et al., (2005) "Sequence-Specific Conjugates of Oligo(2'-O-methylribonucleotides) and Hairpin Oligocarboxamide Minor-Groove Binders: Design, Synthesis, and Binding Studies with Double-Stranded DNA," Chemistry & Biodiversity 2:936952.
Optical Tweezers: Introduction to Optical Tweezers, Retrieved Apr. 21, 2010 from http://www.nbi.dk/~tweezer/introduction.htm, pp. 1-5.
Pablo, P.J., et al., (2000) "Absence of dc-Conductivity." Phys. Rev. Lett. 85:4992-4995.
Partial International Search Report dated Feb. 15, 2010 for PCT/US09/055878, 3 pgs.
Perry, J., et al., (2005) "Review of Fabrication of Nanochannels for Single Phase Liquid Flow," 3rd Intl. Conference on Microchannels and Minichannels, Paper No. ICMM2005-75104.
Pevzner, P., (1989) "1-Tuple DNA Sequencing: Computer Analysis," Journal of Biomolecular Structure & Dynamics 7: pp. 63-64.
Pevzner, P. et al., (1991) "Improved Chips for Sequencing by Hybridization," Journal of Biomolecular Structure & Dynamics 9:399-410.
Powell, M., et al., (1993) "Characterization of the Pf3 Single-Strand DNA Binding Protein by Circular Dichroism Spectroscopy," Biochemistry 32:12538-12547.
Preparata, F., et al., (1999) "On the Power of Universal Bases in Sequencing by Hybridization," 7 pgs.
Preparata, F.P., et. al., (2000) "Sequencing-by-Hybridization at the Information-Theory Bound: An Optimal Algorithm," J. Comp. Biol. 7:621-630.
(2003) "Sequence information can be obtained from single DNA molecules," Proc. Nat. Acad. Sci. USA 100:3960-3964, Braslavsky et al.

(56) References Cited

OTHER PUBLICATIONS

Riehn, R. et al., (2005) "Restriction mapping in nanofluidic devices," Proc. Nat. Acad. Sci., 102:1012-10016.
Robertson, J., et al., (2007) "Single-Molecule Mass Spectrometry in Solution Using a Solitary Nanopore," PNAS 104:8207-8211.
Rucker, V.C., et al., (2003) "Sequence Specific Fluorescence Detection of Double Strand DNA," J. Am. Chem. Soc. 125:1195-1202.
Sanger, F. et al., (1977) "DNA Sequencing with Chain-Terminating Inhibitors," Proc. Natl. Acad. Sci. USA 12:5463-5467.
Shinohara. Y., et al., (1995) "Use of a Biosensor Based on Surface Plasmon Resonance and Biotinyl Glycans for Analysis of Sugar Binding Specificities of Lectins," J. Biochem, 117:1076-1082.
Singer, E., (2008) "The $100 Genome," Technology Review 4 pgs.
Smeets, R., et al., (2008) "Translocation of RecA-Coated Double-Stranded DNA through Solid-State Nanopores," Nano Letters pp. A-G.
Southern, E.M., (1996) "DNA Chips: Analysing Sequence by Hybridization to Oligonucleotide on a Large Scale," Trends in Genetics 12(3):110-115.
Storm, et al., (2003) "Fabrication of solid-state nanopores with single-nanometre precision," Nature Materials 2:537-540.
Storm, A., et al., (2005) "Fast DNA Translocation through a Solid-State Nanopore," Nano Letters 5(7):1193-1197.
Strezoska, Z., et al., (1991) "DNA Sequencing by Hybridization: 100 Bases Read by a Non-Gel-Based Method," Proc. Natl. Acad. Sci. USA 88:10089-10093.
Tegenfeldt, J., et al., (2004) "The Dynamics of Genomic-Length DNA Molecules in 100 nm Channels," Proc. Nat. Acad. Sci. USA 101:10979-10983.
Tersoff, (2001) "Less is more," Nature 412, 135-136.
Terwilliger, T., et al., (1996) "Gene V Protein Dimerization and Cooperativity of Binding to Poly (dA)," Biochemistry 35:16652-16664.
Tucker, P., et al., (1994) "Crystal Structure of the Adenovirus DNA Binding Protein a Hook-On Model for Cooperative DNA Binding," The EMBO Journal 13(13):2994-3002.
Urbach, A.R., (2001) "Toward rules for 1:1 polyamide:DNA recognition," PNAS 98:4343-4348.
Warren, C.L., et al., (2006) "Defining the Sequence-Recognition Profile of DNA-Binding Molecules," PNAS 103:867-872.
Warren, S., (1996) "The Expanding World of Trinucleotide Repeats," Science 271:1374-1375.

Web article (2003) "DNA Combed Into Nanochannels," http://www.nature.com.
Written Opinion dated Jul. 1, 2008, PCT/US06/38748, 6 pgs.
Zhang, W., et al., (2006) "Discrimination of Hairpin Polyamides with an $\alpha$-Substituted-$\gamma$-aminobutyric Acid as a 5'-TG-3' Reader in DNA Minor Groove," J. Am. Chem. Soc. 128:8766-8776.
Zwolak, M., et al., (2008) "Colloquium: Physical Approaches to DNA Sequencing and Detection." Rev. Mod. Phy. 80:141-165 (J).
Lysov, Y.P., et al., (1988) "Determination of the Nucleotide Sequence of DNA Using Hybridization with Oligonucleotides. A New Method," Dokl. Acad. Nauk SSSR 303:1508-1511 [Article in Russian], Abstract only.
Examination Report mailed Feb. 7, 2013 in European Application No. 10 717 908.7 -1240 (4 pages).
Examination Report mailed Mar. 4, 2013 in European Application No. 08 835 216.6 -1404 (6 pages).
International Preliminary Report on Patentability in PCT/US2012/024708 mailed Aug. 13, 2013.
International Preliminary Report on Patentability, Application No. PCT/US2011/053274, issuance date May 28, 2013, 14 pages.
International Preliminary Report on Patentability, Application No. PCT/US2011/059933, issuance date May 21, 2013, 8 pages.
International Search Report and Written Opinion dated Jun. 29, 2010, PCT/US09/055876, 13 pages.
Notice of Reasons for Rejection mailed Jun. 17, 2013 in Japanese Patent Application No. 2011-525300.
Notification of the First Office Action mailed Sep. 28, 2012 in Chinese Patent Application No. 200980140663.0.
Notification of the Second Office Action mailed Apr. 2, 2013 in Chinese Patent Application No. 200980140663.0.
Olasagasti, F.; Lieberman, K. R.; Benner, S.; Cherf, G. M.; Dahl, J. M.; Deamer, D. W.; Akeson, M. Nat. Nanotechnol. 2010, 5, 798-806.
Rehrauer, William M. et al., "Alteration of the Nucleoiside Triphosphate (NTP) Catalytic Domain within *Escherichia coli* recA Protein Attenuates NTP Hydrolysis but Not Joint Molecule Formation*", pp. 1292-1297, The Journal of Biological Chemistry, The American Society for Biochemistry and Molecule Biology, Inc., vol. 268, No, 2, Jan. 15, 1993.
Waugh, David S., "Make the most of affinity tags", pp. 316-320, Trends in Biotechnology, Science Direct, vol. 23, No. 6, Jun. 2005.
International Search Report and Written Opinion, PCT/US2011/053274, dated May 2, 2013.

* cited by examiner

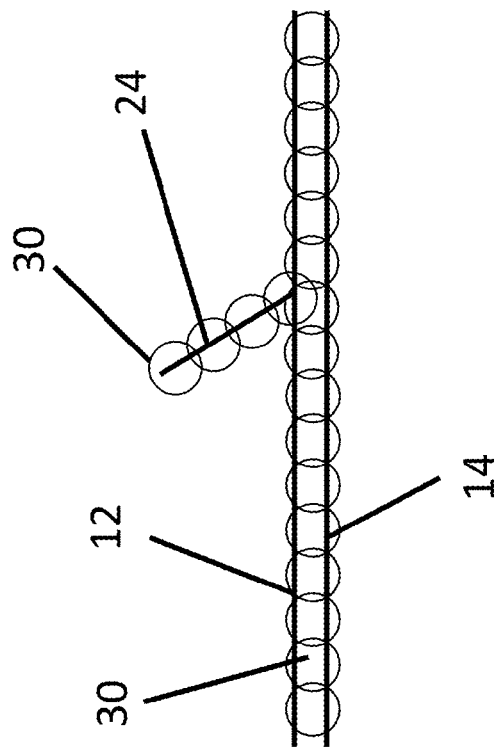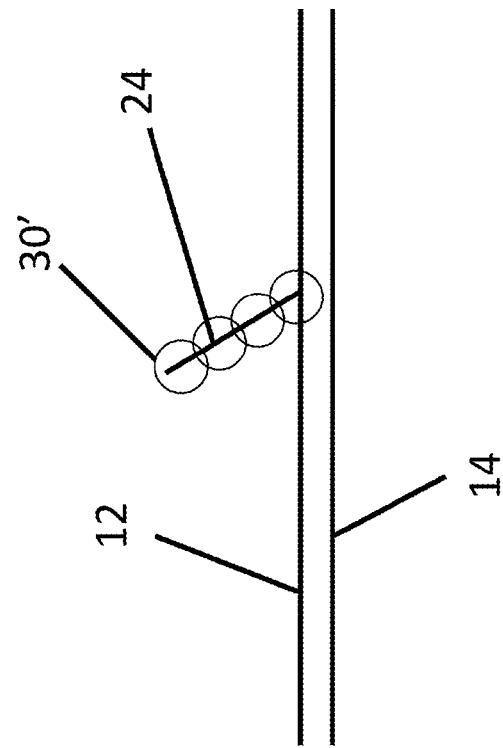
FIG. 4a
FIG. 4b

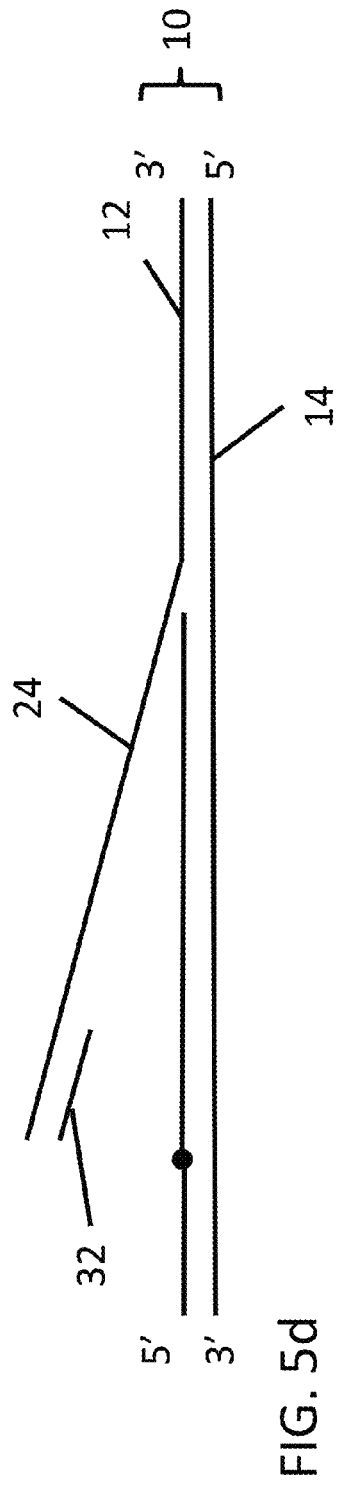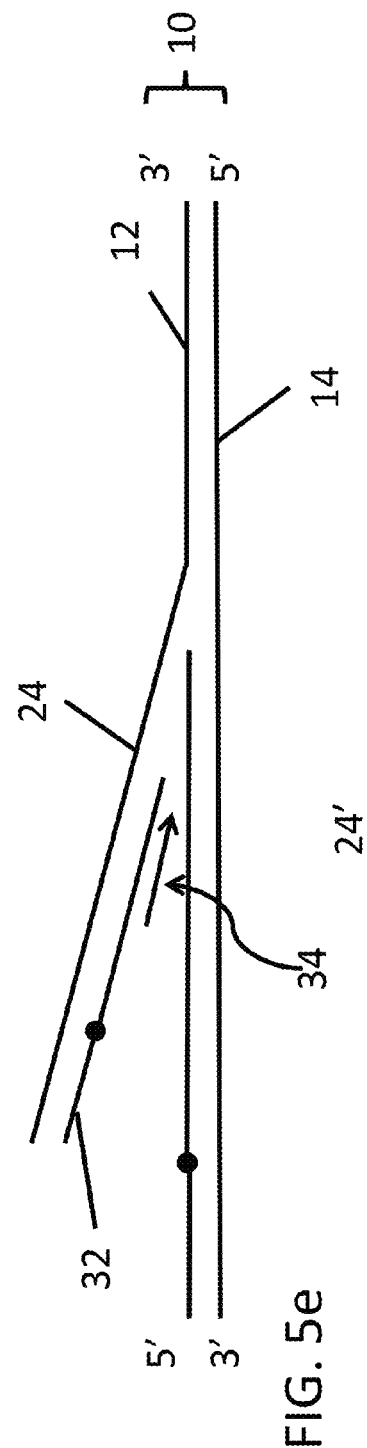

```
                        SEQUENCE LISTING

<160> NUMBER OF SEQ ID NOS: 8

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(10)
<223> OTHER INFORMATION: a, c, t, g, unknown or other

<400> SEQUENCE: 1 ggatcnnnnn                                                                10

<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(5)
<223> OTHER INFORMATION: a, c, t, g, unknown or other

<400> SEQUENCE: 2 nnnnngatcc                                                                10

<210> SEQ ID NO 3
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(10)
<223> OTHER INFORMATION: a, c, t, g, unknown or other

<400> SEQUENCE: 3 gagtcnnnnn                                                                10

<210> SEQ ID NO 4
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(5)
```

```
<223> OTHER INFORMATION: a, c, t, g, unknown or other

<400> SEQUENCE: 4 nnnnngactc                                                              10

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
cttacctcag caggt                                                        15

<210> SEQ ID NO 6
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
acctgctgag gtaag                                                        15

<210> SEQ ID NO 7
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
cttacctcag c                                                            11

<210> SEQ ID NO 8
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8 ttttttttttt ttt                                                         13
```

ASSAY METHODS USING NICKING ENDONUCLEASES

SEQUENCE LISTING

The instant application contains a Sequence Listing which has been submitted in ASCII format via EFS-Web and is hereby incorporated by reference in its entirety. Said ASCII copy, created on Nov. 8, 2010, is named NAB-011.txt and is 2,432 bytes in size.

FIELD OF INVENTION

The present invention relates generally to assay methods and devices for the analysis of biopolymers. Mapping of such biopolymers is contemplated herein.

BACKGROUND

Identifying the composition and sequence of various biomolecules, such as human DNA, with accuracy and specificity is of great interest. Mapping and sequencing technology, however, is time consuming and expensive to develop and implement. For example, sequencing the DNA of a single individual for the Human Genome Project required over $3 billion of funding.

It is estimated that each person's DNA varies from one another by approximately 1 base in 1000. Knowledge of such genetic variations among human populations may allow the scientific community to identify genetic trends that are related to various medical predispositions, conditions, or diseases, and may lead to the realization of truly personalized medicine where treatments are customized for a given individual based on that individual's DNA. A reduction in the time and cost of DNA mapping and sequencing is needed to develop such knowledge and to tailor medical diagnostics and treatments based on the genetic makeup of individual patients.

New DNA sequencing technologies produce many short reads (lengths of sequenced DNA) that are then used to assemble the sequence of the entire sample. These "short-read" technologies have sequenced read lengths of from 25 bases to 400 bases. For genomes of modest size or complexity, these short reads are incapable of correctly assembling the sequence of the sample because of the appearance of repeats in the sequence. DNA mapping may be used to guide the assembly. For instance, restriction maps may be used to aid in the assembly of short-read data. More rapid and higher density maps would be useful to enable short-read technologies to assemble data.

Hybridization Assisted Nanopore Sequencing (HANS) is a nanopore-based method for sequencing genomic lengths of DNA and other biomolecules. The method relies on detecting the position of hybridization of probes on specific portions of the biomolecule to be sequenced or characterized.

In this method, two reservoirs of solution are separated by a nanometer-sized hole, or nanopore, that serves as a fluidic constriction of known dimensions. The application of a constant DC voltage between the two reservoirs results in a baseline ionic current that is measured. If an analyte is introduced into a reservoir, it may pass through the fluidic channel and change the observed current, due to a difference in conductivity between the electrolyte solution and analyte. The magnitude of the change in current depends on the volume of electrolyte displaced by the analyte while it is in the fluidic channel. The duration of the current change is related to the amount of time that the analyte takes to pass through the nanopore constriction. The current signals are used in determining the position of the probes on the biomolecule. Measurement of the probe positions allows for accurate reconstruction of the biomolecule sequence using computer algorithms. A need exists for efficient methods and devices capable of rapid and accurate nucleic acid mapping and sequencing for de novo assembly of human genomes. It is desirable to have long read lengths and to use as little nucleic acid template as possible.

Mapping and sequencing may also be achieved using fluidic nano-channel and micro-channel based devices. In these systems, the analyte is caused to transit through a nano- or micro-channel, and its passage is detected by electrodes positioned along the length of the channel. In one embodiment, described in co-pending U.S. patent application Ser. No. 12/789,817, filed May 28, 2010, and the teachings of which are incorporated herein by reference in its entirety, a first pair of electrodes is positioned longitudinally along the channel to provide a reference voltage between them. A second pair of electrodes is positioned across the channel to define a detection volume. As an analyte passes through the detection volume, it causes a detectable change in an electrical property, for example, a change in the reference voltage. Probes that are hybridized to the analyte cause a further change in the electrical property when they enter the detection volume. Thus, it is possible to detect when the analyte is present in the detection volume, as well as the absolute or relative position of hybridized probes as they enter the detection volume.

Despite the foregoing, there remains a need for improved methods and devices for the analysis of biopolymers, including improved assay methods for mapping and sequencing such biopolymers.

SUMMARY

The embodiments of the invention relate to assay methods for preparing target analyte samples suitable for mapping using nanopore, micro-channel or nano-channel analysis devices.

In one embodiment, the method includes the steps of a) providing a double-stranded DNA template having first and second DNA strands, each strand having a 5' end and a 3' end, b) contacting the double-stranded DNA template with a nicking endonuclease to form a nick at a sequence-specific nicking location on the first DNA strand, c) conducting a base extension reaction on the first DNA strand along the corresponding region of the second DNA strand, the reaction starting at the nick and progressing toward the 3' end of the first DNA strand to thereby form a single-stranded flap on the template adjacent to the nicking location, and d) coating the double-stranded DNA template with a binding moiety that enhances electrical detection of the template and the single-stranded flap, to thereby prepare the target analyte.

In another embodiment, the method includes the steps of a) providing a double-stranded DNA template having first and second DNA strands, each strand having a 5' end and a 3' end, b) contacting the template with a nicking endonuclease to form nicks at sequence-specific locations on the first DNA strand, c) conducting a first base extension reaction on the first DNA strand along the corresponding region of the second DNA strand, the reaction starting at each nick and progressing toward the 3' end of the first DNA strand to thereby form single-stranded flap regions on the double-stranded DNA template adjacent to the sequence specific nicking locations, and d) conducting a second base extension reaction on at least one flap region to form at least one double-stranded flap, to thereby prepare the target analyte. In this embodiment, all or a portion of the resulting analyte may be coated with a binding moiety. Thus, in this embodiment, an additional step of coating the double-stranded flap, as well as the double-stranded DNA template, with a binding moiety may be employed.

In still another embodiment, the method includes the steps of a) providing a double-stranded DNA template having a first and a second DNA strand, each DNA strand having a 5' end and a 3' end, b) contacting the double-stranded DNA template with a nicking endonuclease to form a nick at a sequence-specific nicking location on the first DNA strand, c) conducting a base extension reaction on the first DNA strand along a corresponding region of the second DNA strand, the reaction starting at the nick and progressing toward the 3' end of the first DNA strand to thereby form a single-stranded flap on the double-stranded DNA template adjacent to the sequence-specific nicking location, and d) coating the single-stranded flap with a binding moiety that selectively binds with single-stranded DNA to enhance electrical detection of the single-stranded flap, to thereby prepare the target analyte.

In another embodiment, the method includes the steps of a) providing a double-stranded DNA template having first and second DNA strands, each strand having a 5' end and a 3' end, b) contacting the template with a nicking endonuclease to form nicks at sequence-specific locations on the first DNA strand, c) conducting a first base extension reaction on the first DNA strand along the corresponding region of the second DNA strand, the reaction starting at each nick and progressing toward the 3' end of the first DNA strand to thereby form single-stranded flap regions on the double-stranded DNA template adjacent to the sequence-specific nicking locations, d) conducting a second base extension reaction on at least one single-stranded flap region to form at least one double-stranded flap, e) adding a single-stranded extension to the double-stranded flap, and f) hybridizing one or more probes to the single-stranded extension, to thereby prepare the target analyte. The single stranded extension may be at least 100 bases in length, and may comprise a polyT or polyA polymers. The extension may be added to the double-stranded flap using a terminal transferase. The probes may be tagged with gold particles and may comprise polyA oligomers (in the case of a polyT extension), or polyT oligomers (in the case of a polyA extension).

In each embodiment above, the biomolecule to be analyzed may be double-stranded DNA. The nicking endonucleases may be Nb.BbvCI, Nb.BsmI, NbBsrDI, Nb.BtsI, Nt.AlwI, Nt.BbvCI, Nt.BsmAI, Nt.BspQI, Nt.BstNBI, and Nt.CviPII, used either alone or in various combinations; however, any nicking endonuclease may be employed, either alone or in combination. Base extension reactions may be achieved by contacting a DNA strand with a polymerase, one or more nucleotides, a ligase, or any combination thereof. The binding moiety may be a protein. Examples of suitable proteins include RecA, T4 gene 32 protein, f1 geneV protein, human replication protein A, Pf3 single-stranded binding protein, adenovirus DNA binding protein, and *E. coli* single-stranded binding protein.

Further embodiments of the invention relate to target analytes comprising double-stranded DNA fragments having one or more double-stranded DNA flaps, and target analytes comprising double-stranded DNA fragments having one or more single- or double-stranded DNA flaps that have been coated with a binding moiety. DNA fragments having one or more double-stranded flaps with single-stranded extensions are contemplated as well. The extensions may be hybridized with oligonucleotide probes, and the probes may include tags such as gold particles.

The target analytes prepared by the methods of the present invention are configured for the detection of positional information in a nanopore system, as well as in a fluidic channel system employing nano-channels or micro-channels. As such, embodiments of the invention relate to monitoring changes in an electrical property across a nanopore or a fluidic channel as the target analytes made using the methods described above are translocated through the nanopore or fluidic channel. The monitored changes are indicative of double-stranded regions of the target analyte as well as flap regions. Further, embodiments of the invention relate to using the detected changes in the electrical property to differentiate between double-stranded and flap regions on the target analyte. The differentiation may be used to determine nick locations and thereby map at least a portion of the DNA template.

Thus, in one embodiment, the present invention relates to the method of a) providing a double-stranded DNA template having first and second DNA strands, each strand having a 5' end and a 3' end, b) contacting the double-stranded DNA template with a nicking endonuclease to form a nick at a sequence-specific nicking location on the first DNA strand, c) conducting a base extension reaction on the first DNA strand along the corresponding region of the second DNA strand, the reaction starting at the nick and progressing toward the 3' end of the first DNA strand to thereby form a single-stranded flap on the template adjacent to the nicking location, d) coating the double-stranded DNA template with a binding moiety that enhances electrical detection of the template and the single-stranded flap, to thereby prepare the target analyte, and e) monitoring changes in an electrical property as the target analyte is translocated through a nanopore or across a fluidic micro- or nano-channel, where the changes in the electrical property are indicative of double-stranded regions of the target analyte and of the single-stranded flap regions. The additional step of differentiating between the double-stranded template and single-stranded flap regions, based at least in part, on detected changes in the electrical property, to determine nick locations and map at least a portion of the double-stranded DNA template may be employed as well.

In another embodiment, the present invention relates to the method of a) providing a double-stranded DNA template having first and second DNA strands, each strand having a 5' end and a 3' end, b) contacting the template with a nicking endonuclease to form nicks at sequence-specific locations on the first DNA strand, c) conducting a first base extension reaction on the first DNA strand along the corresponding region of the second DNA strand, the reaction starting at each nick and progressing toward the 3' end of the first DNA strand to thereby form single-stranded flap regions on the double-stranded DNA template adjacent to the sequence specific nicking locations, d) conducting a second base extension reaction on at least one flap region to form at least one double-stranded flap, to thereby prepare the target analyte, and e) monitoring changes in an electrical property as the target analyte is translocated through a nanopore or across a fluidic micro- or nano-channel, where the changes in the electrical property are indicative of double-stranded regions of the target analyte and of the double-stranded flap regions. The additional step of differentiating between the double-stranded template and double-stranded flap regions, based at least in part, on detected changes in the electrical property, to determine nick locations and map at least a portion of the double-stranded DNA template may be employed as well.

In still another embodiment, the method includes the steps of a) providing a double-stranded DNA template having a first and a second DNA strand, each DNA strand having a 5' end and a 3' end, b) contacting the double-stranded DNA template with a nicking endonuclease to form a nick at a sequence-specific nicking location on the first DNA strand, c) conducting a base extension reaction on the first DNA strand along a corresponding region of the second DNA strand, the reaction starting at the nick and progressing toward the 3' end of the first DNA strand to thereby form a single-stranded flap on the double-stranded DNA template adjacent to the sequence-specific nicking location, d) coating the single-stranded flap with a binding moiety that selectively binds with single-stranded DNA to enhance electrical detection of the single-stranded flap, to thereby prepare the target analyte, and e) monitoring changes in an electrical property as the target analyte is translocated through a nanopore or across a fluidic micro- or nano-channel, where the changes in the electrical property are indicative of double-stranded regions of the target analyte and of the single-stranded flap regions. The additional step of differentiating between the double-stranded template and single-stranded flap regions, based at least in part, on detected changes in the electrical property, to determine nick locations and map at least a portion of the double-stranded DNA template may be employed as well.

In another embodiment, the method includes the steps of a) providing a double-stranded DNA template having first and second DNA strands, each strand having a 5' end and a 3' end, b) contacting the template with a nicking endonuclease to form nicks at sequence-specific locations on the first DNA strand, c) conducting a first base extension reaction on the first DNA strand along the corresponding region of the second DNA strand, the reaction starting at each nick and progressing toward the 3' end of the first DNA strand to thereby form single-stranded flap regions on the double-stranded DNA template adjacent to the sequence-specific nicking locations, d) conducting a second base extension reaction on at least one single-stranded flap region to form at least one double-stranded flap, e) adding a single-stranded extension to the double-stranded flap, and f) hybridizing one or more probes to the single-stranded extension, to thereby prepare the target analyte. Changes in an electrical property may be monitored as the target analyte is translocated through a nanopore or across a fluidic micro- or nano-channel, where the changes in the electrical property are indicative of double-stranded regions of the target analyte and of the extended flap regions. The additional step of differentiating between the double-stranded template and extended flap regions, based at least in part, on detected changes in the electrical property, to determine nick locations and map at least a portion of the double-stranded DNA template may be employed as well.

In another embodiment, the method includes the steps of a) providing a double-stranded DNA template having first and second DNA strands, each strand having a 5' end and a 3' end, b) contacting the double-stranded DNA template with a nicking endonuclease to form a nick at a sequence-specific nicking location on the first DNA strand, c) conducting a base extension reaction on the first DNA strand along the corresponding region of the second DNA strand, the reaction starting at the nick and progressing toward the 3' end of the first DNA strand to thereby form a single-stranded flap on the template adjacent to the nicking location, and d) monitoring changes in an electrical property as the target analyte is translocated through a nanopore or across a fluidic micro- or nano-channel, where the changes in the electrical property are indicative of double-stranded regions of the target analyte and of the single-stranded flap regions. The additional step of differentiating between the double-stranded template and single-stranded flap regions, based at least in part, on detected changes in the electrical property, to determine nick locations and map at least a portion of the double-stranded DNA template may be employed as well.

As before, in each embodiment above, the biomolecule to be analyzed may be double-stranded DNA. The nicking endonucleases may be Nb.BbvCI, Nb.BsmI, NbBsrDI, Nb.BtsI, Nt.AlwI, Nt.BbvCI, Nt.BsmAI, Nt.BspQI, Nt.BstNBI, and Nt.CviPII, used either alone or in various combinations; however, any nicking endonuclease may be employed, either alone or in combination. Base extension reactions may be achieved by contacting a DNA strand with a polymerase, one or more nucleotides, a ligase, or any combination thereof. If used, the binding moiety may be a protein. Examples of suitable proteins include RecA, T4 gene 32 protein, f1 geneV protein, human replication protein A, Pf3 single-stranded binding protein, adenovirus DNA binding protein, and *E. coli* single-stranded binding protein.

In cases where a single-stranded extension is formed on a double-stranded flap region, the single stranded extension may be at least 100 bases in length, and may comprise a polyT or polyA polymers. The extension may be added to the double-stranded flap using a terminal transferase. The probes may be tagged, for example, with gold particles and may comprise polyA oligomers (in the case of a polyT extension), or polyT oligomers (in the case of a polyA extension).

BRIEF DESCRIPTION OF THE FIGURES

FIG. 4a is a schematic depiction of the DNA molecule of FIG. 3 subsequent to contact of the molecule with a binding moiety that binds to single- and double-stranded DNA.

FIG. 4b is a schematic depiction of the DNA molecule of FIG. 3 subsequent to contact of the molecule with a binding moiety that preferentially binds to single-stranded DNA.

FIG. 5d is a schematic depiction of a DNA molecule subsequent to hybridization of an oligonucleotide probe to the flap.

FIG. 5e is a schematic depiction of a DNA molecule subsequent to a second base extension reaction to form a double-stranded flap.

FIG. 5f is a schematic depiction of a DNA molecule having a double-stranded flap.

FIG. 8b is a schematic depiction of a current measurement waveform as a DNA molecule having a flap translocates through the nanopore apparatus of FIG. 8a.

DETAILED DESCRIPTION

As used in this description and the accompanying claims, the following terms shall have the meanings given, unless the context indicates otherwise:

An "analyte" or "target" means a double-stranded DNA biomolecule.

A "DNA template" means a DNA molecule that serves as a pattern for the synthesis of an additional molecular structure.

A "binding moiety" means an entity, such as a protein, capable of providing a coating on an analyte.

An "endonuclease" is an enzyme that cleaves the phosphodiester bond within a polynucleotide chain, in contrast with an exonuclease, which cleaves phosphodiester bonds at the end of a polynucleotide chain.

A "restriction endonuclease" or "restriction enzyme" cleaves DNA at specific sites.

A "nicking endonuclease" or "nickase" is a form of restriction endonuclease. Restriction endonucleases recognize specific nucleotide sequences in double-stranded DNA and generally cleave both strands. Some sequence-specific endonucleases, however, cleave only one of the strands. These endonucleases are known as nicking endonucleases.

The translocation of biomolecules and biomolecule/protein complexes through a nanopore, a nano-channel or a micro-channel sequencing system may include detecting an electrical signal indicative of the passage of the biomolecule through the system, as well as an electrical signal indicative of the passage of single- or double-stranded flaps formed on the biomolecule through the system. The biomolecule and/or the flaps may be coated with a binding moiety such as a protein. The time for translocation may be indicative of the length of the biomolecule. The detection step may discriminate between coated, uncoated, or multiply coated regions, as a coated region may have a signal about ten times that of an uncoated region. Increasing the signal-to-noise ratio may increase confidence in the detection of flaps formed on the biomolecule. Positional information of flaps on the target biomolecule may be used to identify nicking sites, and thereby facilitates the mapping of the biomolecule.

Figure 1:
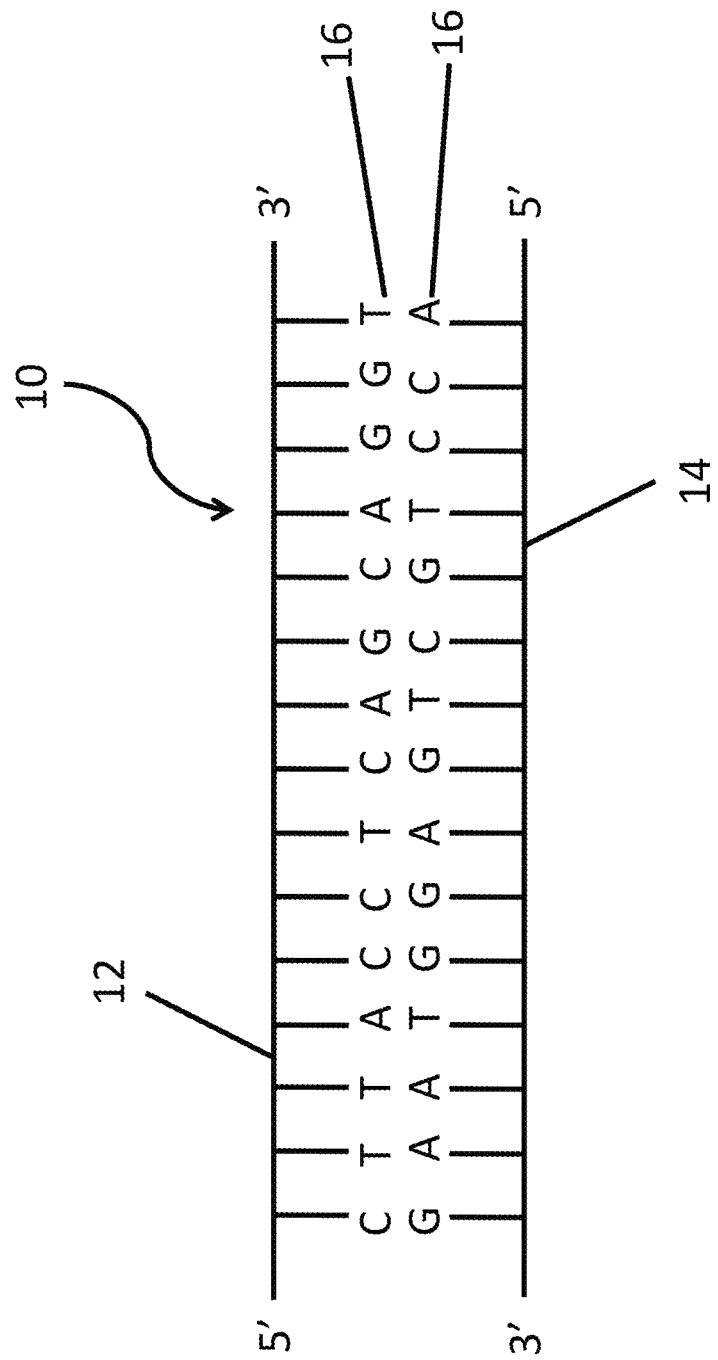
FIG. 1 is a schematic depiction of a DNA molecule (SEQ ID NOS 5-6, respectively, in order of appearance).

Referring to FIG. 1, a DNA molecule 10, e.g., a double-stranded DNA template, is schematically depicted. The molecule 10 comprises two DNA strands, e.g., first and second strands 12, 14 positioned in anti-parallel relation to one another. The two DNA strands may also be referred to as top and bottom strands 12, 14. Each of the two opposing strands 12, 14 may be sequentially formed from repeating groups of nucleotides 16 where each nucleotide 16 consists of a phosphate group, 2-deoxyribose sugar and one of four nitrogen-containing bases. The nitrogen-containing bases include cytosine (C), adenine (A), guanine (G) and thymine (T). Each DNA strand has a 5' end and a 3' end. In particular, the DNA strands 12, 14 are read in a particular direction, from the top (called the 5' or "five prime" end) to the bottom (called the 3' or "three prime" end). Similarly, RNA molecules are polynucleotide chains, which differ from those of DNA by having ribose sugar instead of deoxyribose and uracil bases (U) instead of thymine bases (T).

The bases in the molecules do not share an equal affinity for one another. Thymine (T) bases favor binding with adenine (A) bases, while cytosine (C) bases favor binding with guanine (G) bases. Binding is mediated via hydrogen bonds that exist between the opposing base pairs. For example, base A binds to base T using two hydrogen bonds, while base C binds to base G using three hydrogen bonds.

Nicking endonucleases useful in embodiments of the present invention include Nb.BbvCI, Nb.BsmI, NbBsrDI, Nb.BtsI, Nt.AlwI, Nt.BbvCI, Nt.BsmAI, Nt.BspQI, Nt.BstNBI, and Nt.CviPII, used either alone or in various combinations. As noted above, nickases are sequence-specific endonucleases which are characterized in that they cleave only one strand of double-stranded DNA at the recognition site.

The nickase Nb.BbvCI is derived from an *E. coli* strain expressing an altered form of the BbvCI restriction genes [Ra+:Rb(E177G)] from *Bacillus brevis*. It nicks at the following recognition site (with "^" specifying the nicking site and "N" representing any one of C, A, G or T):

```
5'. . .C C T C A G C. . .3'

3'. . .G G A G T^C G. . .5'
```

The nickase Nb.BsmI is derived from an *E. coli* strain that carries the cloned BsmI gene from *Bacillus stearothermophilus* NUB 36. It nicks at the following recognition site:

```
5'. . .G A A T G C N. . .3'
3'. . .C T T A C̆ G N. . .5'
```

The nickase Nb.BsrDI is derived from an *E. coli* strain expressing only the large subunit of the BsrDI restriction gene from *Bacillus stearothermophilus* D70. It nicks at the following recognition site:

```
5'. . .G C A A T G N N. . .3'
3'. . .C G T T A C̆ N N. . .5'
```

The nickase Nb.BtsI is derived from an *E. coli* strain expressing only the large subunit of the BtsI restriction gene from *Bacillus thermoglucosidasius*. It nicks at the following recognition site:

```
5'. . .G C A G T G N N. . .3'
3'. . .C G T C A C̆ N N. . .5'
```

The nickase Nt.AlwI is an engineered derivative of AlwI which catalyzes a single-strand break four bases beyond the 3' end of the recognition sequence on the top strand. It is derived from an *E. coli* strain containing a chimeric gene encoding the DNA recognition domain of AlwI and the cleavage/dimerization domain of Nt.BstNBI. It nicks at the following recognition site:

```
5'. . .G G A T C N N N N̆ N. . .3'   (SEQ ID NO: 1)
3'. . .C C T A G N N N N N. . .5'    (SEQ ID NO: 2)
```

The nickase Nt.BbvCI is derived from an *E. coli* strain expressing an altered form of the BbvCI restriction genes [Ra(K169E):Rb+] from *Bacillus brevis*. It nicks at the following recognition site:

```
5'. . .C C̆ T C A G C. . .3'
3'. . .G G A G T C G. . .5'
```

The nickase Nt.BsmAI is derived from an *E. coli* strain expressing an altered form of the BsmAI restriction genes from *Bacillus stearothermophilus* A664. It nicks at the following recognition site:

```
5'. . .G T C T C N̆ N. . .3'
3'. . .C A G A G N N. . .5'
```

The nickase Nt.BspQI is derived from an *E. coli* strain expressing an engineered BspQI variant from BspQI restriction enzyme. It nicks at the following recognition site:

```
5'. . .G C T C T T C N̆. . .3'
3'. . .C G A G A A G N. . .5'
```

The nickase Nt.BstNBI catalyzes a single strand break four bases beyond the 3' side of the recognition sequence. It is derived from an *E. coli* strain that carries the cloned Nt.BstNBI gene from *Bacillus stereothermophilus* 33M. It nicks at the following recognition site:

```
5'. . .G A G T C N N N N N̆. . .3'   (SEQ ID NO: 3)
3'. . .C T C A G N N N N N. . .5'    (SEQ ID NO: 4)
```

The nickase Nt.CviPII cleaves one strand of DNA of a double-stranded DNA substrate. The final product on pUC19 (a plasmid cloning vector) is an array of bands from 25 to 200 base pairs. CCT is cut less efficiently than CCG and CCA, and some of the CCT sites remain uncleaved. It is derived from an *E. coli* strain that expresses a fusion of Mxe GyrA intein, chitin-binding domain and a truncated form of the Nt.CviPII nicking endonuclease gene from Chlorella virus NYs-1. It nicks at the following recognition site:

```
5'. . .C̆ C D. . .3'
3'. . .G G H. . .5'
```

Each of the restriction endonucleases described above is available from New England Biolabs of Ipswich, Mass.

It should be understood that the invention is not intended to be limited to the nicking endonucleases described above; rather, it is anticipated that any endonuclease capable of providing a nick in a double-stranded DNA molecule may be used in accordance with the methods of the present invention.

Figures 2A, 2B:
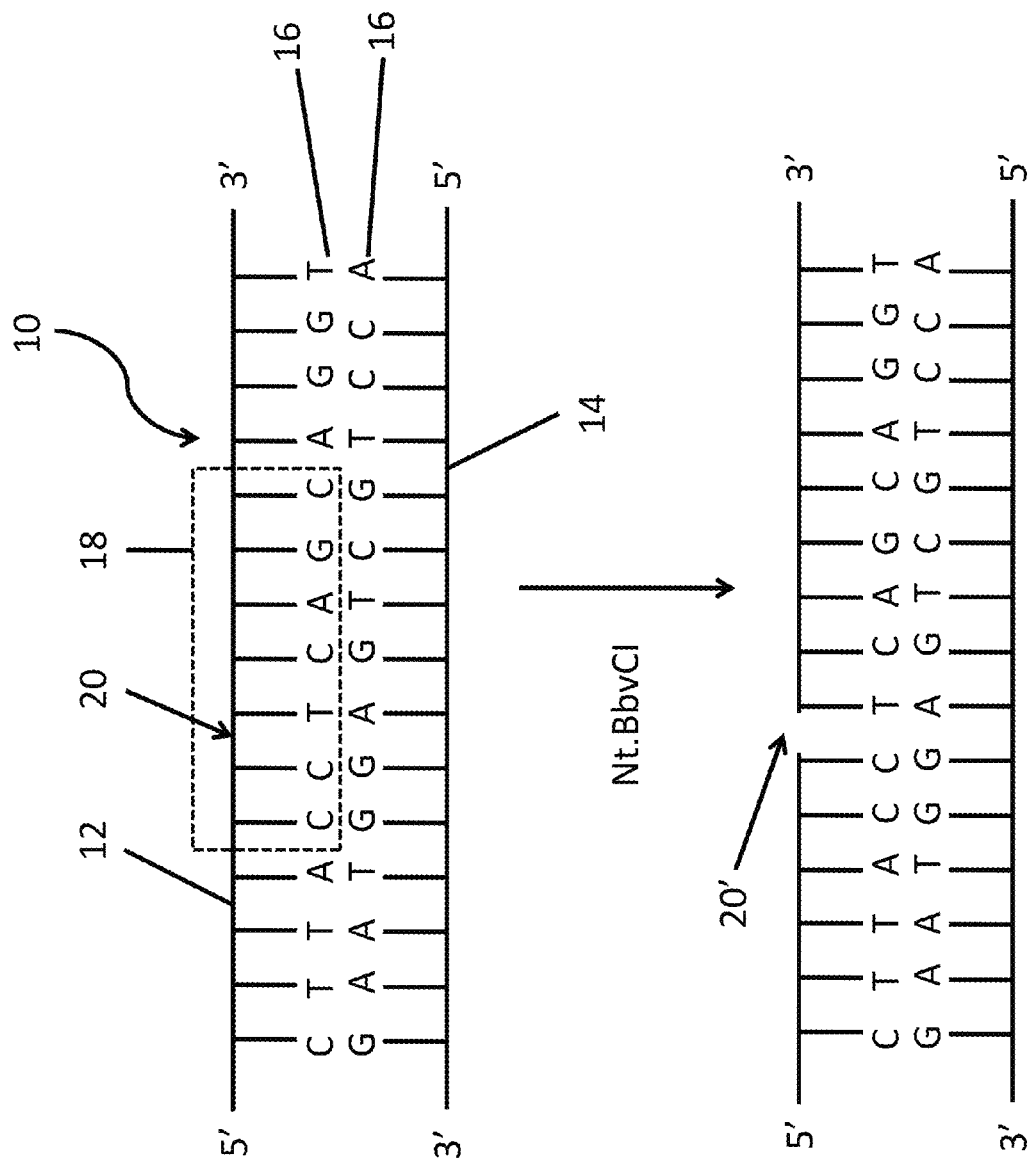
FIG. 2a is a schematic depiction of a DNA molecule (SEQ ID NOS 5-6, respectively, in order of appearance) showing the recognition and nicking site for the nicking endonuclease Nt.BbvCI.
FIG. 2b is a schematic depiction of a DNA molecule (bottom strand is disclosed as SEQ ID NO: 6) subsequent to reaction with the nicking endonuclease Nt.BbvCI.

One embodiment of the present invention is depicted in FIGS. 2a-4a or 4b. In FIG. 2a, the DNA molecule 10 of FIG. 1 is shown. The recognition sequence of the nicking endonuclease Nt.BbvCI is indicated by the boxed area 18, and the specific nicking site 20 of that nicking endonuclease is identified. The double-stranded DNA template is contacted with the nicking endonuclease. In FIG. 2b, the nicking endonuclease Nt.BbvCI has cleaved the top strand of the DNA molecule leaving a nick 20' at a sequence-specific nicking location on the top DNA strand 12.

Figure 3:
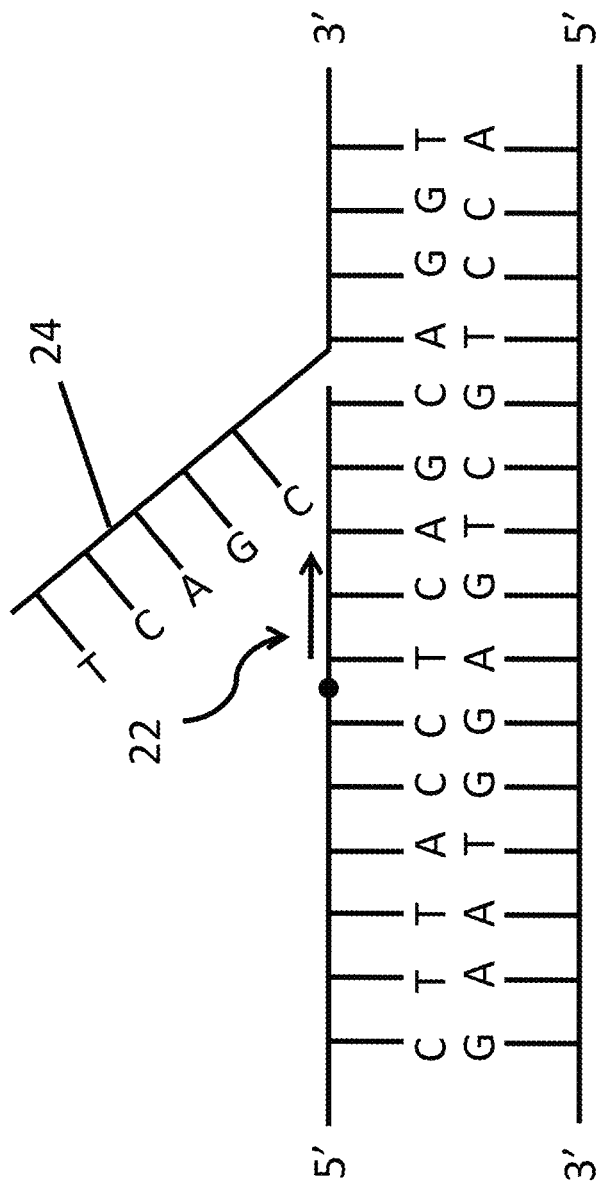
FIG. 3 is a schematic depiction of a nicked DNA molecule (SEQ ID NOS 7 and 6, respectively, in order of appearance) subsequent to a base extension reaction beginning at the nicking site.

As shown in FIG. 3, a base extension reaction 22, such as a primer extension reaction, utilizing for example, a polymerase, one or more nucleotides, a ligase, or any combination thereof is carried out beginning at the nick site (indicated by a dot). The base extension reaction is conducted on the top DNA strand along (and pursuant to) the corresponding region of the bottom DNA strand. In such reactions, that form a nucleic acid complementary to a nucleic acid template, a primer complementary to a single-stranded DNA template is typically employed. Starting at the primer, a DNA polymerase may be used to add mononucleotides complementary to the template at the 3' end of the primer. Various base extension reactions will be familiar to those of ordinary skill in the art. As the base extension reaction progresses toward the 3' end of the top strand, a flap 24 of single-stranded DNA is formed from the original top strand of the DNA molecule. The flap 24 is single-stranded, and is adjacent to the sequence-specific nicking location. The base extension reaction is allowed to proceed until the flap 24 has reached a desired length, resulting in the formation of a target analyte including the double-stranded DNA molecule and a flap. The presence of the flap aids in the detection via, for example, HANS, or other nanopore-, nanochannel-, or microchannel-based detection techniques. In one embodiment, it is preferred that the flap 24 be at least one hundred (100) bases in length, however, the invention is not intended to be limited as such.

Finally, as shown in FIGS. 4a and 4b, a binding moiety may be used to coat the DNA molecule or portions thereof. In FIG. 4a, the binding moiety 30 has been used to coat both strands 12, 14 of the DNA molecule as well as the single-stranded flap 24. Alternatively, as shown in FIG. 4b, a binding moiety 30' having a preference for single-stranded DNA has been used to coat only the single-stranded flap formed on the DNA molecule via the method described above.

The binding moiety 30 may include or consist essentially of a protein or other composition which binds to single- and/or double-stranded DNA. In one embodiment, the binding moiety is the protein RecA. The binding moiety may enhance electrical detection of the double-stranded DNA template and flap via, for example, HANS, or other nanopore-, nanochannel-, or microchannel-based detection techniques.

Protein RecA from *E. coli* typically binds single- or double-stranded DNA in a cooperative fashion to form filaments containing the DNA in a core and an external sheath of protein (McEntee, K.; Weinstock, G. M.; Lehman, I. R. Binding of the RecA Protein of *Escherichia coli* to Single- and Double-Stranded DNA. *J. Biol. Chem.* 1981, 256, 8835, incorporated by reference herein in its entirety). DNA has a diameter of about 2 nm, while DNA coated with RecA has a diameter of about 10 nm. The persistence length of the DNA increases to around 950 nm, in contrast to 0.75 nm for single-stranded DNA or 50 nm for double-stranded DNA. T4 gene 32 protein is known to cooperatively bind single-stranded DNA (Alberts, B. M.; Frey, L. T4 Bacteriophage Gene32: A Structural Protein in the Replication and Recombination of DNA. *Nature,* 1970, 227, 1313-1318, incorporated by reference herein in its entirety). *E. coli* single-stranded binding protein binds single-stranded DNA in several forms depending on salt and magnesium concentrations (Lohman, T. M.; Ferrari, M. E. *Escherichia Coli* Single-Stranded DNA-Binding Protein: Multiple DNA-Binding Modes and Cooperativities. *Ann. Rev. Biochem.* 1994, 63, 527-570, incorporated by reference herein in its entirety). The *E. coli* single-stranded binding protein may form a varied coating on the biomolecule. The f1 geneV protein is known to coat single-stranded DNA (Terwilliger, T. C. Gene V Protein Dimerization and Cooperativity of Binding of poly(dA). *Biochemistry* 1996, 35, 16652, incorporated by reference herein in its entirety), as is human replication protein A (Kim, C.; Snyder, R. O.; Wold, M. S. Binding properties of replication protein A from human and yeast cells. *Mol. Cell. Biol.* 1992, 12, 3050, incorporated by reference herein in its entirety), Pf3 single-stranded binding protein (Powell, M. D.; Gray, D. M. Characterization of the Pf3 single-strand DNA binding protein by circular dichroism spectroscopy. *Biochemistry* 1993, 32, 12538, incorporated by reference herein in its entirety), and adenovirus DNA binding protein (Tucker, P. A.; Tsernoglou, D.; Tucker, A. D.; Coenjaerts, F. E. J.; Leenders, H.; Vliet, P. C. Crystal structure of the adenovirus DNA binding protein reveals a hook-on model for cooperative DNA binding. *EMBO J.* 1994, 13, 2994, incorporated by reference herein in its entirety). The protein-coated DNA may then be translocated through a nanopore as has been demonstrated with RecA bound to double-stranded DNA (Smeets, R. M. M.; Kowalczyk, S. W.; Hall, A. R.; Dekker, N. H.; Dekker, C. Translocation of RecA-Coated Double-Stranded DNA through Solid-State Nanopores. Nano Lett. 2009, incorporated by reference herein in its entirety). The protein coating functions in the same manner for single-stranded DNA regions and double-stranded DNA regions.

In another embodiment of the present invention, the flap formed by the base extension reaction illustrated in FIG. 3 may be converted from a single-stranded flap to a double-stranded flap. In this embodiment, prior to contacting the target analyte with the binding moiety, the single-stranded flap is exposed to a random selection of oligomer probes with the expectation that at least one will hybridize with a portion of the flap and act as a primer. Following such hybridization, a base extension reaction is carried out to cause the flap to become double-stranded.

Figure 5A:
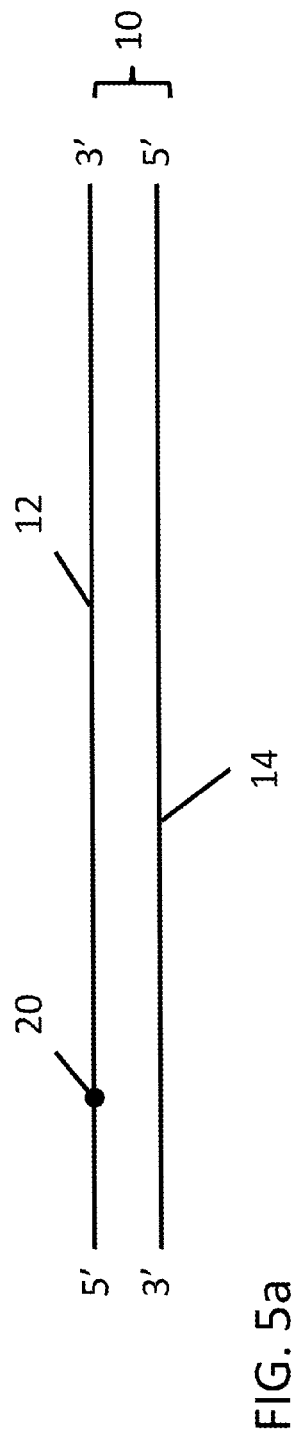
FIG. 5a is a schematic depiction of a DNA molecule showing a recognition and nicking site for a nicking endonuclease.
Figure 5B:
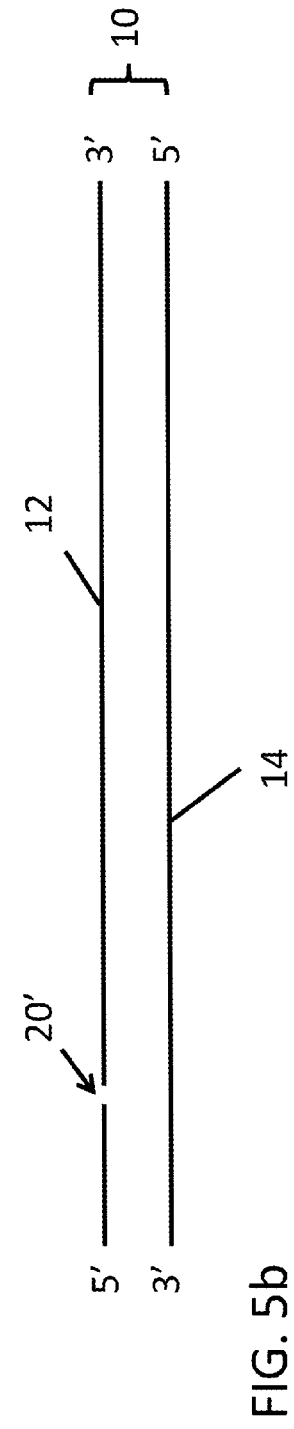
FIG. 5b is a schematic depiction of a DNA molecule subsequent to reaction with a nicking endonuclease.

More specifically, a double-stranded DNA molecule 10 having first and second DNA strands 12, 14 is shown in FIG. 5a. The DNA molecule 10 has a recognition sequence that identifies a nicking site 20 for a preselected nicking endonuclease. As shown in FIG. 5b, upon exposure to the nicking endonuclease, a nick 20' is formed on the DNA molecule 10, i.e., on sequence-specific location on the first DNA strand. By using a predetermined nicking endonuclease with a known recognition sequence, if the site of the nick can be identified, the location of specific recognition sequence can be determined, thereby allowing the molecule to be mapped.

Figure 5C:
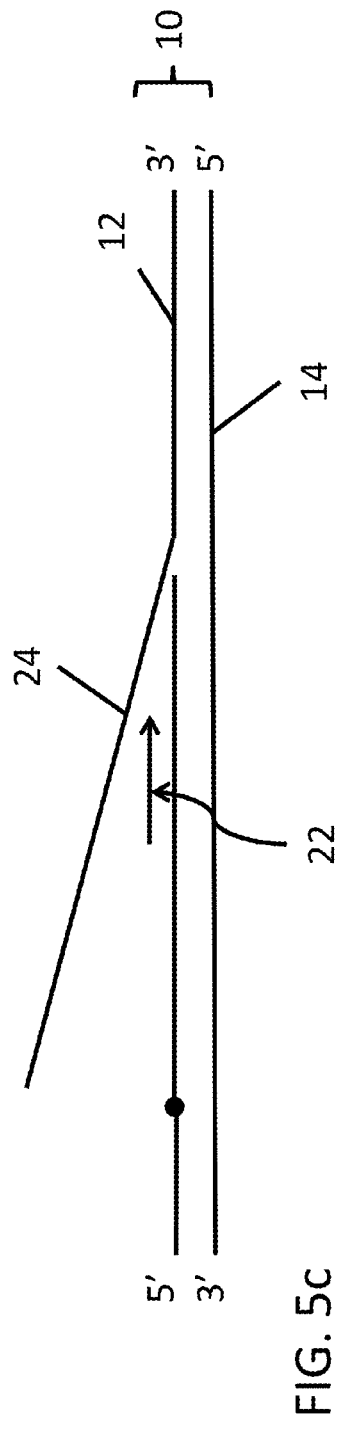
FIG. 5c is a schematic depiction of a nicked DNA molecule subsequent to a first base extension reaction to form a flap.

Following nick 20' formation, a first base extension reaction 22, beginning at the nick site, (indicated by a dot), is carried out. FIG. 5c shows that as the base extension reaction proceeds toward the 3' end of the top strand, a flap 24 of single-stranded DNA is formed from the original top strand of the DNA molecule. The base extension reaction is allowed to proceed until the flap 24 has reached a desired length. In one embodiment, it is preferred that the flap 24 be at least one hundred (100) bases in length, however as discussed with respect to FIG. 3, the invention is not intended to be limited as such.

In FIG. 5d, the flap 24 is exposed to a random selection of oligonucleotide probes. The identity of the probes need not be known; rather, it is the expectation that at least one such probe 32 will hybridize to a portion of the flap 24 to act as a primer forming a site at which a second base extension 34 may be carried out as shown in FIG. 5e. The second base extension can be performed by contacting the flap with a polymerase, one or more nucleotides, a ligase, or any combination thereof. The resulting target analyte 50 comprising a double-stranded DNA base 10 with a double-stranded flap 24' is depicted in FIG. 5f.

Figure 6:
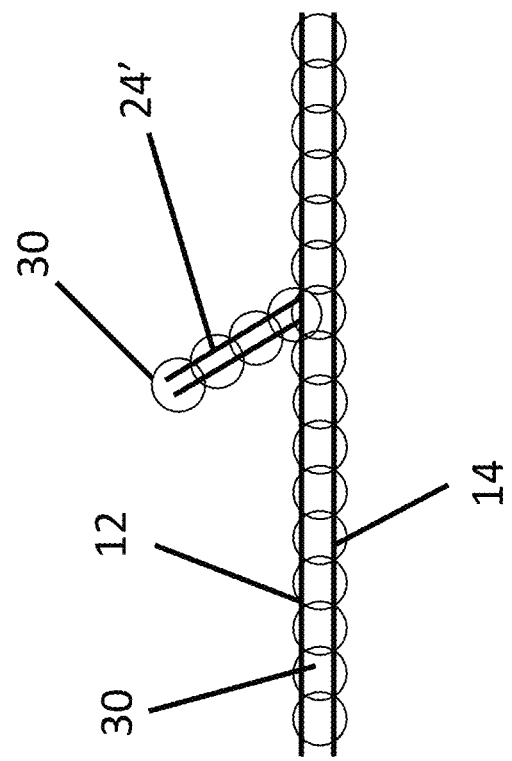
FIG. 6 is a schematic depiction of the DNA molecule of FIG. 5f subsequent to contact of the molecule with a binding moiety.

In FIG. 6, a binding moiety 30 has been used to coat both strands 12, 14 of the DNA molecule as well as the double-stranded flap 24'. As in the previous embodiments, the binding moiety 30 may be a protein or other composition which binds to single- and double-stranded DNA, such as the protein RecA, T4 gene 32 protein, f1 geneV protein, human replication protein A, Pf3 single-stranded binding protein, adenovirus DNA binding protein, and *E. coli* single-stranded binding protein. The binding moiety enhances electrical detection of the target analyte.

In some instances, the recognition and nicking sites may be spaced relatively closely together. In these instances, use of the methods described above may result in small, less readily detectable flaps. Since the flap is formed by the single strand between nicks, if the nicks are closely spaced, flap length is limited. Furthermore, in these instances, if the base extension which results in the flap is allowed to proceed too far, the single strand will be excised entirely from the analyte, resulting in the loss of the flap and thereby the data it provides. A solution to this problem is depicted in FIGS. 7a-7g.

Figure 7A:
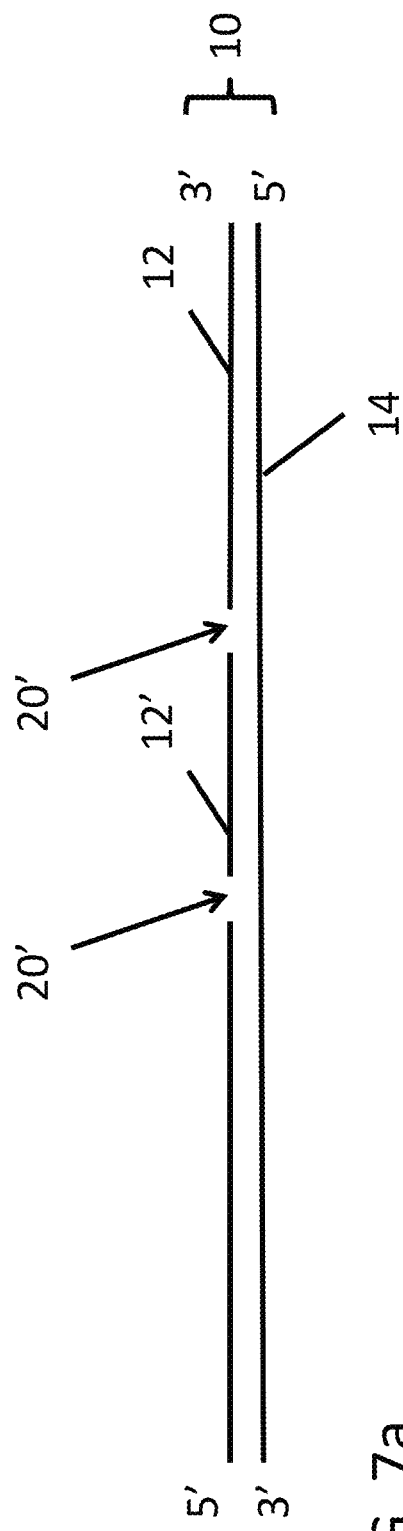
FIG. 7a is a schematic depiction of a DNA molecule having a plurality of closely-spaced recognition and nicking sites subsequent to reaction with a nicking endonuclease.

FIG. 7a depicts a DNA molecule 10 having first 12 and second 14 strands. Strand 12 has been reacted with a nicking endonuclease which created closely-spaced nicks 20'. A short segment of single-stranded DNA 12', which will form one flap, is positioned between the nicks.

Figure 7B:
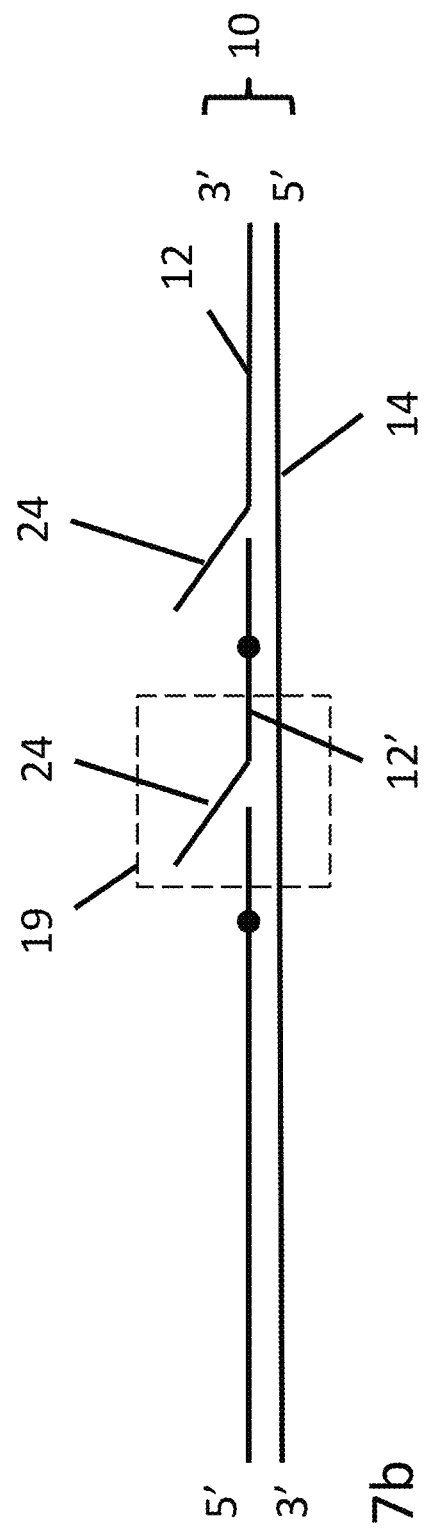
FIG. 7b is a schematic depiction of the DNA molecule of FIG. 7a subsequent to a first base extension reaction to form a plurality of flaps.

In FIG. 7b, a base extension reaction has been carried out to form flaps 24 at each of the nicks. Due to the close spacing between the nicks, the base extension reaction is preferably terminated before segment 12' is excised entirely from the molecule. As a result, a short flap, which is harder to detect, is formed. Furthermore, since the base extension is not isolated to the single short flap of segment 12', but rather, applies to the entire molecule, the early termination of the base extension results in all flaps being small and less readily detectable. The boxed area 19 is used to indicate the portion of the molecule containing one flap that is depicted in FIGS. 7c-7g.

Figure 7C:
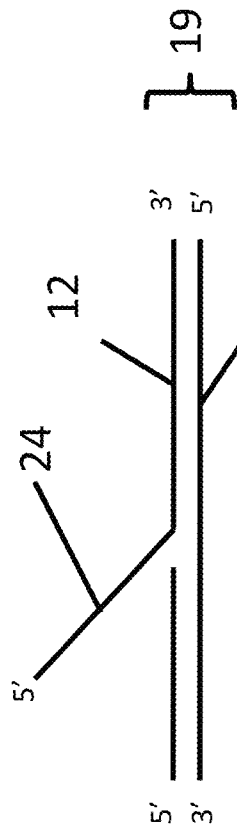
FIG. 7c is a schematic depiction a portion of the DNA molecule of FIG. 7b depicting an isolation of a single flap.

FIG. 7c depicts a single short flap 24 (isolation from box 19) following termination of the base extension.

Figure 7D:
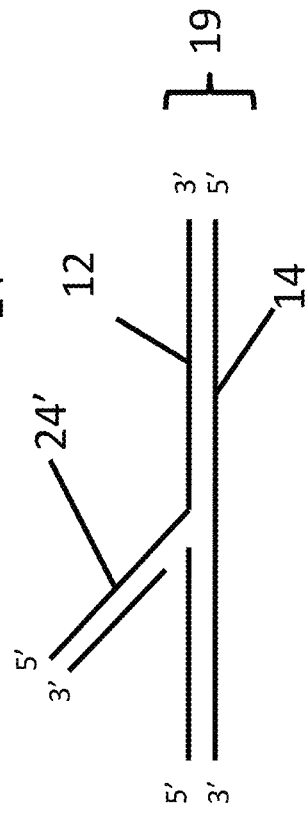
FIG. 7d is a schematic depiction of the portion of the DNA molecule of FIG. 7c subsequent to hybridization of the flap with a probe and use of a base extension reaction to convert the flap into double-stranded DNA.

In FIG. 7d, a double-stranded flap 24' is depicted. This double-stranded flap has been formed using the method shown in FIG. 5e. Specifically, the single-stranded flap has been exposed to a random selection of oligonucleotide probes, and one such probe hybridized to the flap and acted as a primer, allowing a second base extension to be carried out. The result is formation of a short, double-stranded flap 24'.

Figure 7E:
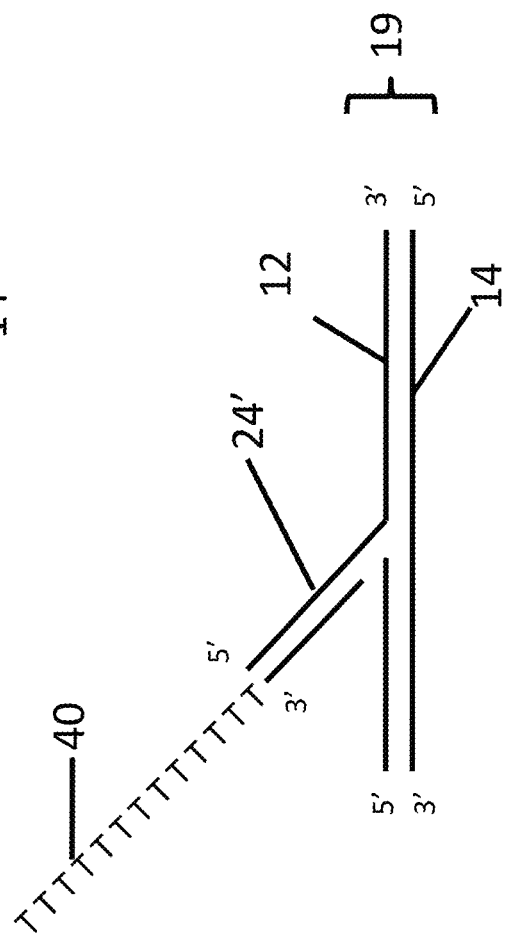
FIG. 7e is a schematic depiction of the portion of the DNA molecule (SEQ ID NO: 8) of FIG. 7d subsequent to the addition of a single-stranded extension to the flap.

FIG. 7e depicts the molecule of FIG. 7d following an extension of the flap. Specifically, following the base extension reaction which formed the double-stranded probe, the molecule is reacted with a terminal transferase to allow extension of the double-stranded flap. The extension 40 occurs on the strand having an exposed 3' end. While any sequence could be extended from the flap 24', it a preferable to form the extension as a polymer of a single base, with polyA and polyT extensions preferred. In the embodiment of FIG. 7e, a polyT extension is shown, however, the invention is not intended to be limited as such. Regardless of the specific sequence of the extension, it may be any length desirable for detection, with lengths of several hundred bases preferred.

Figure 7F:
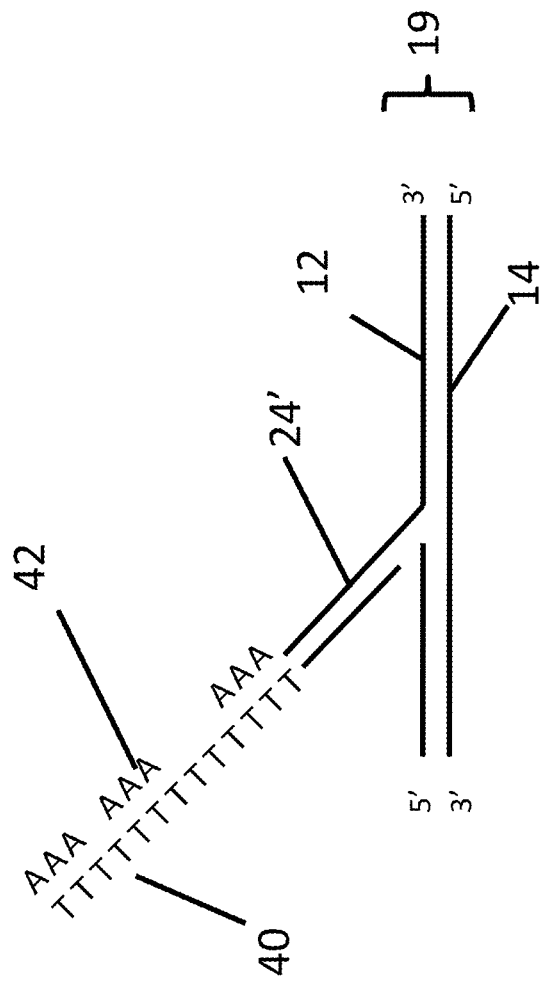
FIG. 7f is a schematic depiction of the portion of the DNA molecule (SEQ ID NO: 8) of FIG. 7e subsequent to hybridization of the extension with complementary oligonucleotide probes.
Figure 7G:
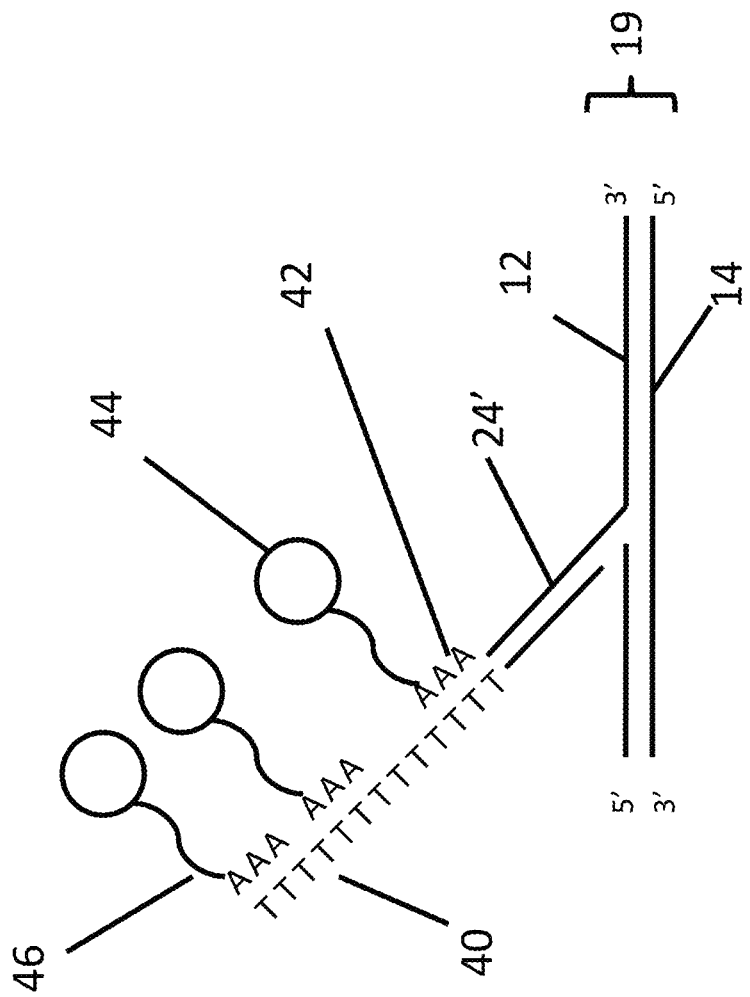
FIG. 7g is a schematic depiction of the portion of the DNA molecule (SEQ ID NO: 8) of FIG. 7e subsequent to hybridization of the extension with tagged complementary oligonucleotide probes.

As a result of the extensions formed on the flaps, detection of the flaps using the methods described below is enhanced as compared to short flaps lacking such extensions. Further enhancements to flap and molecule detection are envisioned as well. For example, the molecule may be reacted with a binding moiety using the methods outlined in FIGS. 4a and 4b. Alternatively, tagged probes may be hybridized to the extensions. Thus, as shown in FIG. 7f, oligonucleotide probes having specificity to the sequence of the extension may be employed. In FIG. 7f, the polyT extension 40 is hybridized with complementary polyA oligonucleotide probes 42. As shown in FIG. 7g, these probes 42 may be provided with tags 44 connected to the probes 42 by a linker 46. While any of a wide variety of tags may be employed, in one preferred embodiment, the tags 44 comprise gold beads. It is intended that the tags will enhance detection of the flaps formed at each of the original nicking sites. Regardless of the enhancement method used, the principle is the same; i.e., detection of the flaps allows determination of the relative position of the original nicking sites. Since the particular nicking endonuclease used to form the nicks is known, determination of the identity and relative location of the nicking sites is enabled.

The target analytes described herein may be configured for detection of positional information in a nanopore and/or a fluidic channel, i.e., a micro-channel or nano-channel system. Mapping of target analytes may be carried out using electrical detection methods employing nanopores, nano-channels or micro-channels using the methods described in U.S. patent application Ser. No. 12/789,817, filed May 28, 2010, the teachings of which have previously been incorporated herein by reference. It is contemplated that such methods may be applied to uncoated analytes having single- or double-stranded flaps, or to analytes having single- or double-stranded flaps where one or both of the base molecule and the single- or double-stranded flap is coated with a binding moiety.

Figure 8A:
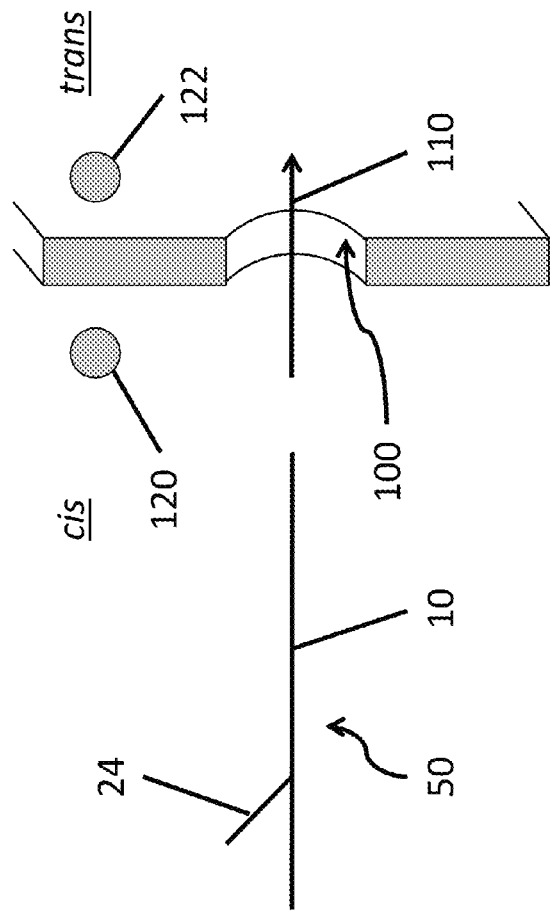
FIG. 8a is a schematic depiction of a DNA molecule having a flap in a nanopore apparatus.

In one embodiment, current across a nanopore is measured during translocation of a DNA strand through the nanopore as shown in FIG. 8a. When used in embodiments of the present invention, a nanopore may have a diameter selected from a range of about 1 nm to about 1 μm. More preferably the nanopore has a diameter that is between about 2.3 nm and about 100 nm. Even more preferably the nanopore has a diameter that is between about 2.3 nm and about 50 nm. Changes in an electrical property across a nanopore may be monitored as the target analyte is translocated therethrough, with changes in the electrical property being indicative of double-stranded regions of the target analyte and of the single-stranded or double-stranded flap regions.

Specifically, for nanopore 100, a measurable current produced by electrodes 120, 122 runs parallel 110 to the movement of the target analyte 50, i.e., a DNA molecule having a flap 24. Variations in current are a result of the relative diameter of the target analyte 50 as it passes through the nanopore 100. This relative increase in volume of the target analyte 50 passing through the nanopore 100 causes a temporary interruption or decrease in the current flow through the nanopore, resulting in a measurable current variation. Portions of the target analyte 50 including a flap 24 are larger in diameter than portions of the target analyte that do not include a flap. As a result, when the flap 24 passes through the nanopore 100, further interruptions or decreases in the current flow between electrodes 120, 122 occurs. These changes in current flow are depicted in the waveform 200 in FIG. 8b.

Figure 8B:
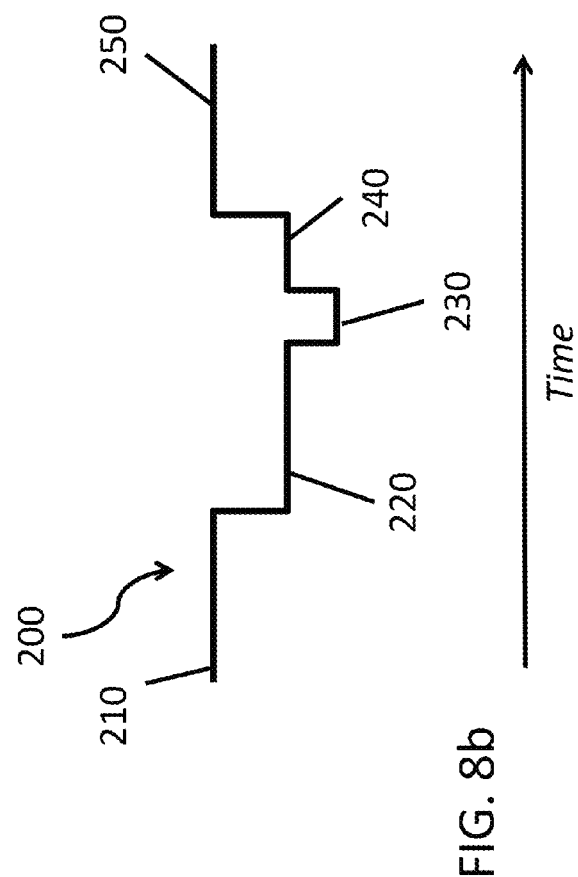

Analysis of the waveform 200 permits differentiation between double-stranded and flap regions of the target analyte based, at least in part, on the detected changes in the electrical property, to thereby determine nick locations and map at least a portion of the double-stranded DNA template. In FIG. 8b, the waveform 200 depicts the changes in a detected electrical property as the target analyte passes through the nanopore, and may be interpreted as follows. Current measurement 210 represents measured current prior to passage of the DNA molecule 10 having a flap formed thereon, i.e., the target analyte, through the nanopore 100 from the cis side to the trans side. As the target analyte enters the nanopore 100, from the cis side of the nanopore, the current is partially interrupted forming a first trough 220 in the recorded current. Once the flap 24 of the target analyte enters the nanopore 100, a further decrease in current occurs, causing a deeper, second trough 230 in the current measurement. Upon passage of the flap 24 entirely through the nanopore 100, a distal portion of the target analyte may remain in the nanopore. This causes the measured current 240 to rise to approximately the level of the first trough 220. Finally, once the entire target analyte has passed completely through the nanopore 100 to the trans side, the measured current 250 returns to a level approximating that of the initial level 210. The current variation measurements are recorded as a function of time. As a result, the periodic variations in current indicate where, as a function of relative or absolute position, the flaps 24 are formed on the target analyte 10. Since the flaps are formed at recognition sites for the specific nicking endonucleases used in flap formation, the relative or absolute position of the specific sequences associated with the recognition site for the particular nicking endonuclease employed may be determined. This allows mapping of those specific sequences on the target analyte. Multiple maps produced using multiple nicking endonucleases may be generated.

The use of a binding moiety, such as the protein RecA, may further enhance detection of target analytes and flap regions on target analytes because the added bulk of the binding moiety coating causes greater current deflections.

Figure 9:
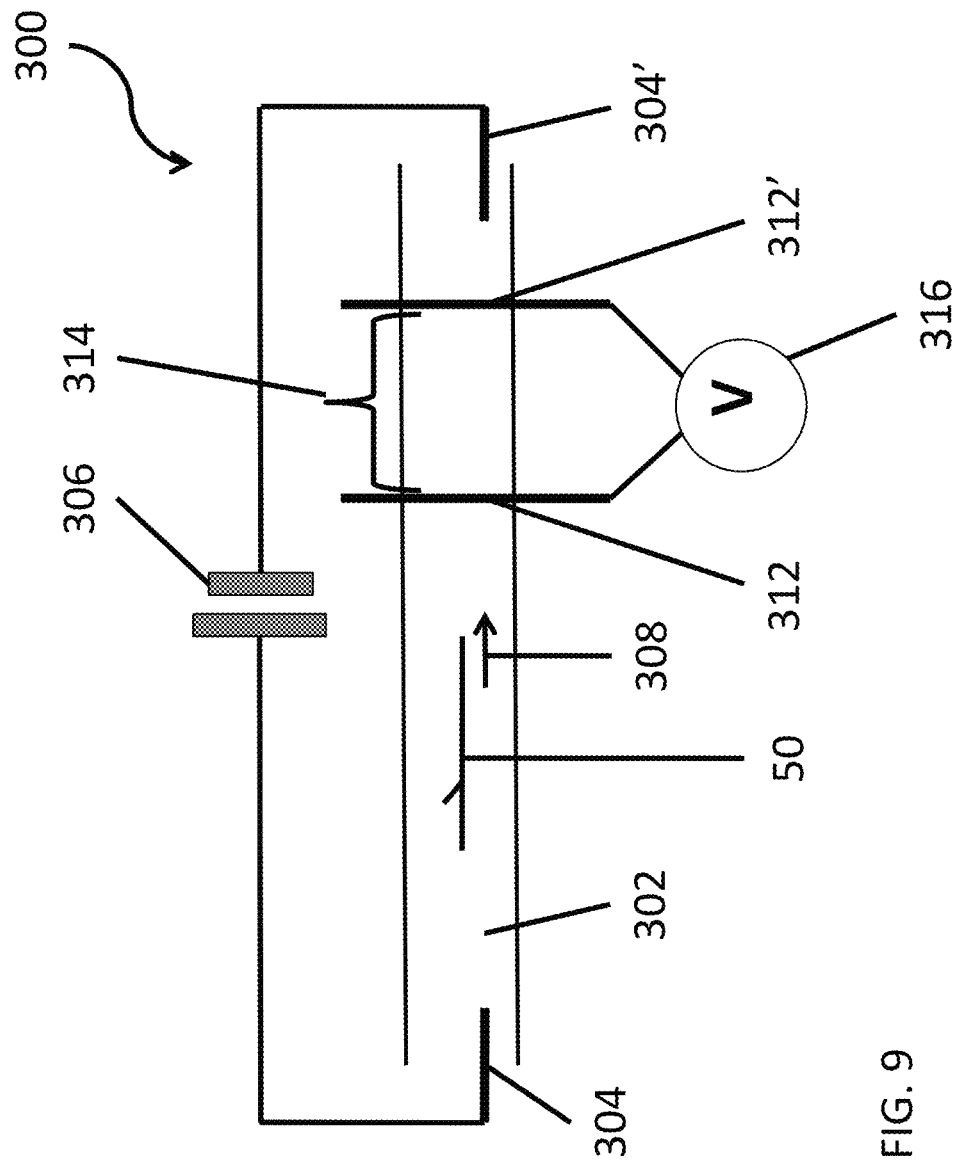
FIG. 9 is a schematic depiction of a fluidic channel apparatus useful for mapping the analytes of the present invention, in which the fluidic channel may be a nano-channel or a micro-channel.
Figure 10A:
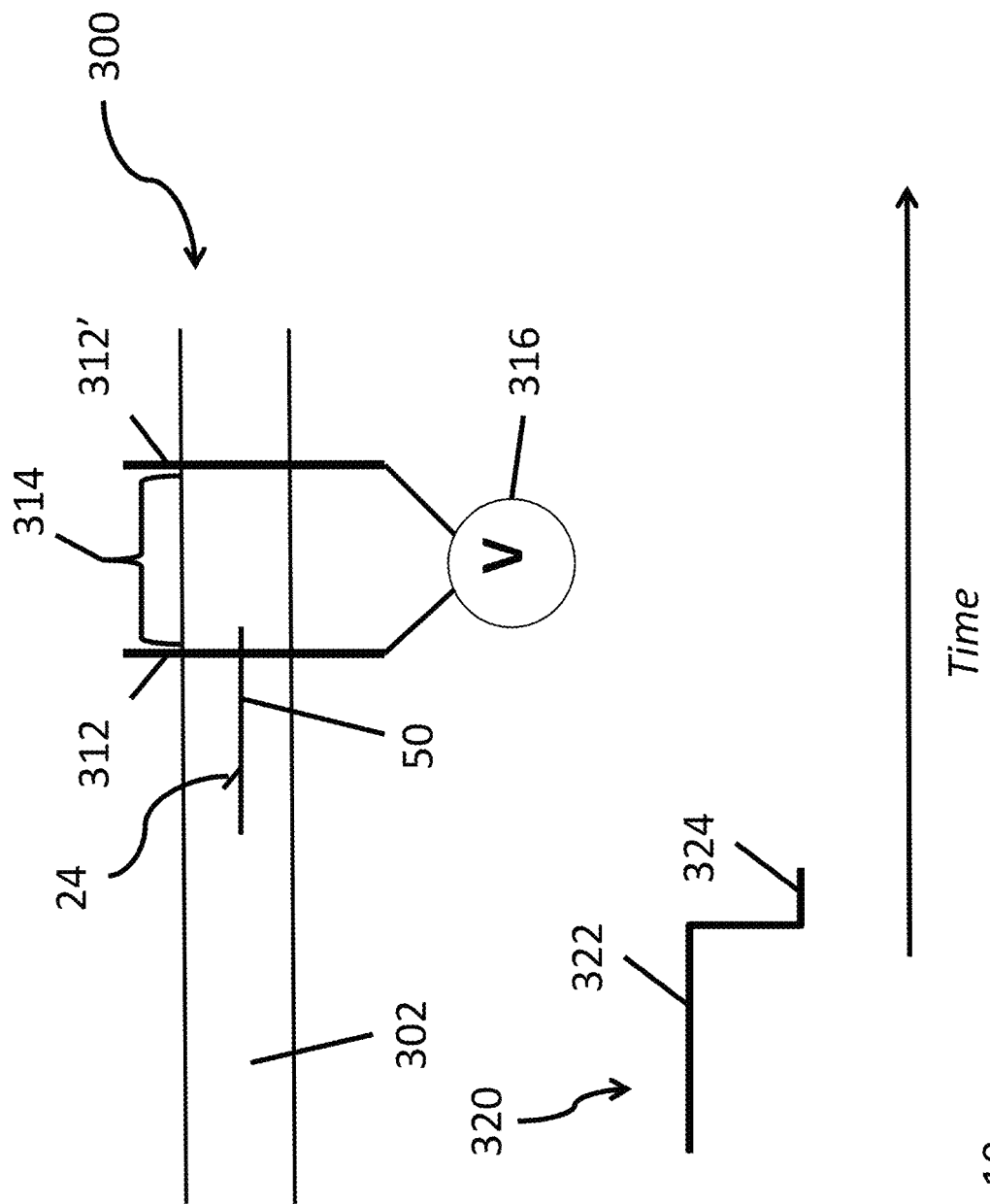
FIG. 10a is a schematic depiction of an electrical potential measurement as a DNA molecule having a flap enters a detection volume in the apparatus of FIG. 9.
Figure 10B:
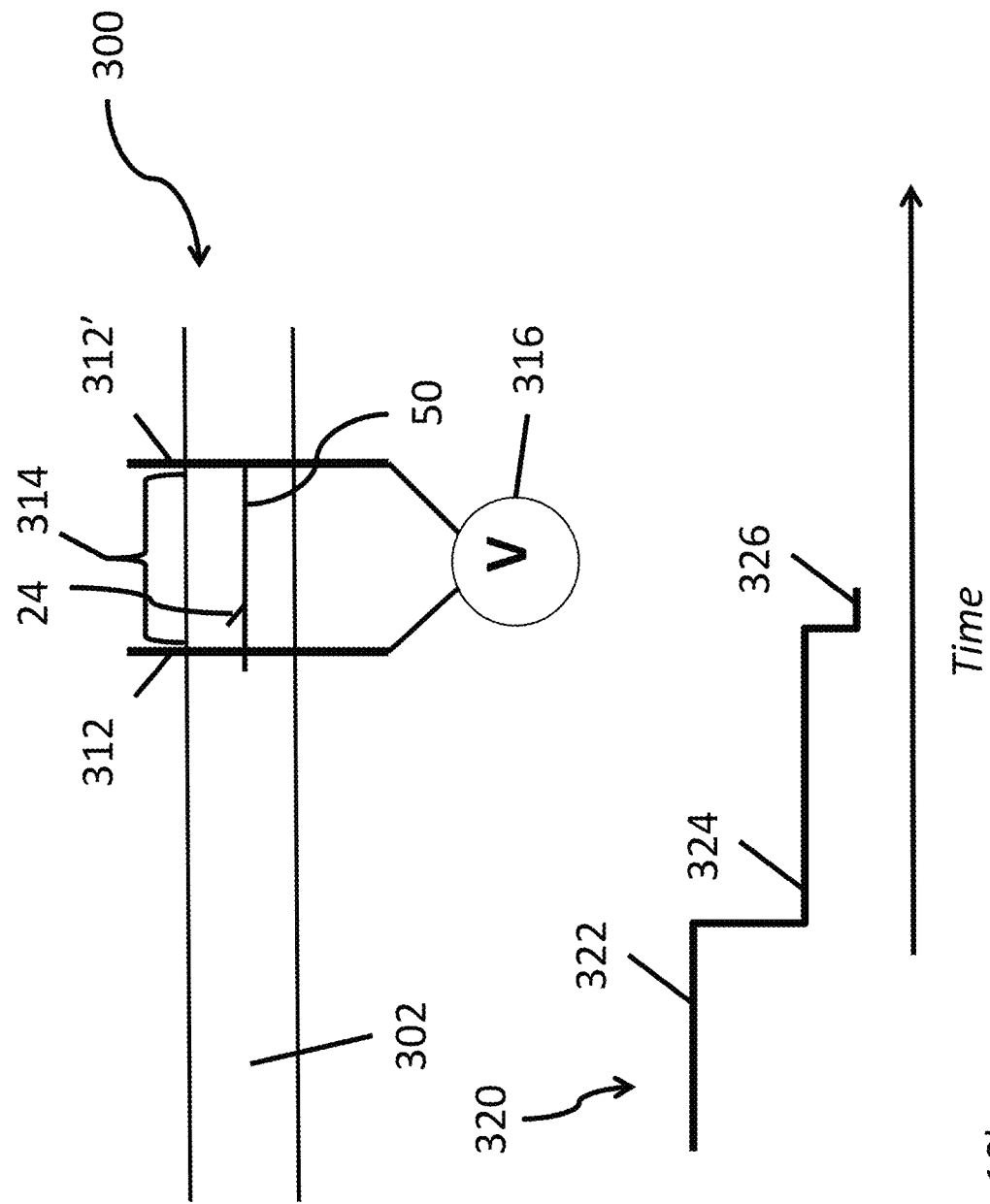
FIG. 10b is a schematic depiction of an electrical potential measurement as a flap on a DNA molecule enters a detection volume in the apparatus of FIG. 9.
Figure 10C:
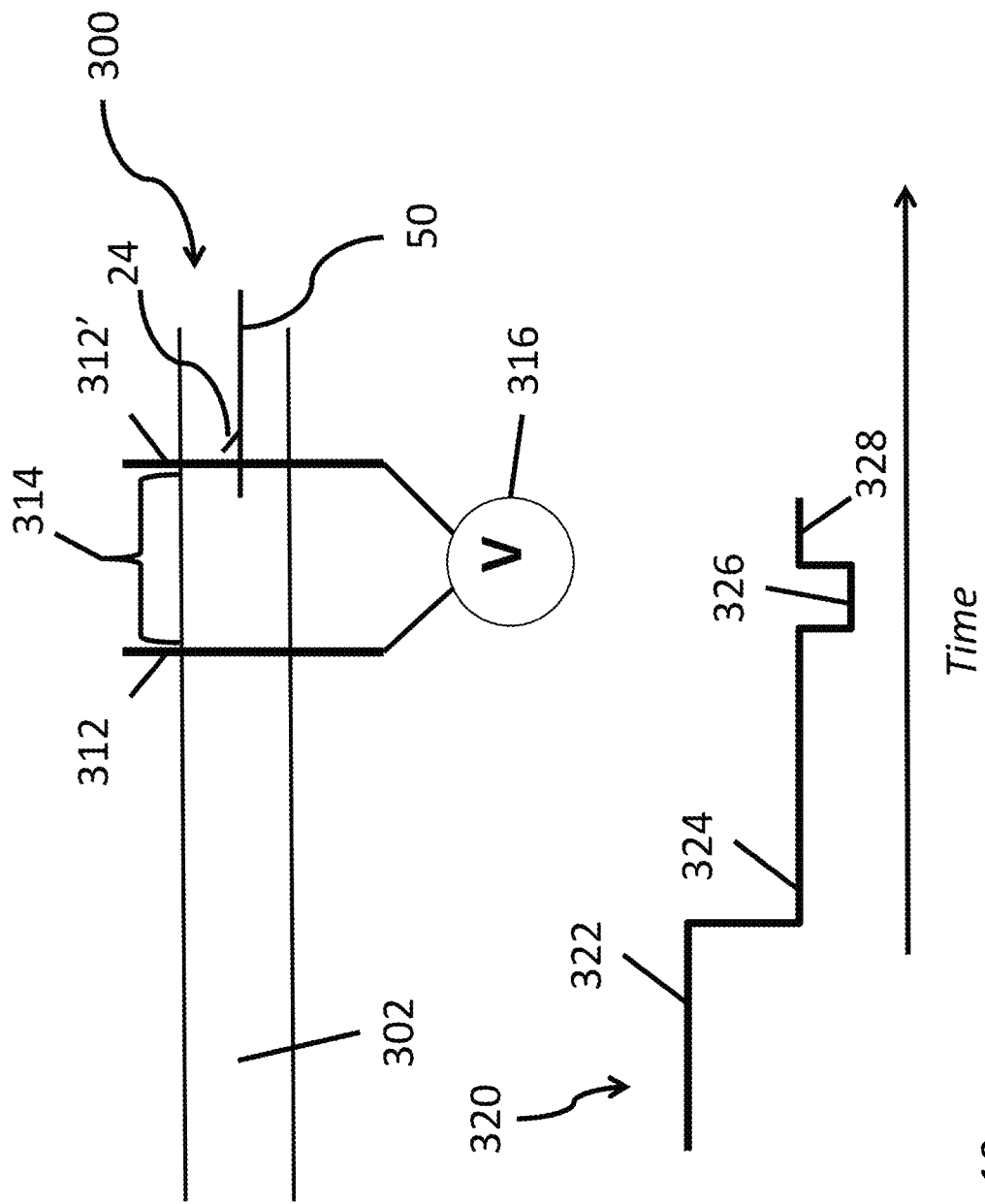
FIG. 10c is a schematic depiction of an electrical potential measurement as a flap on a DNA molecule exits a detection volume in the apparatus of FIG. 9.
Figure 10D:
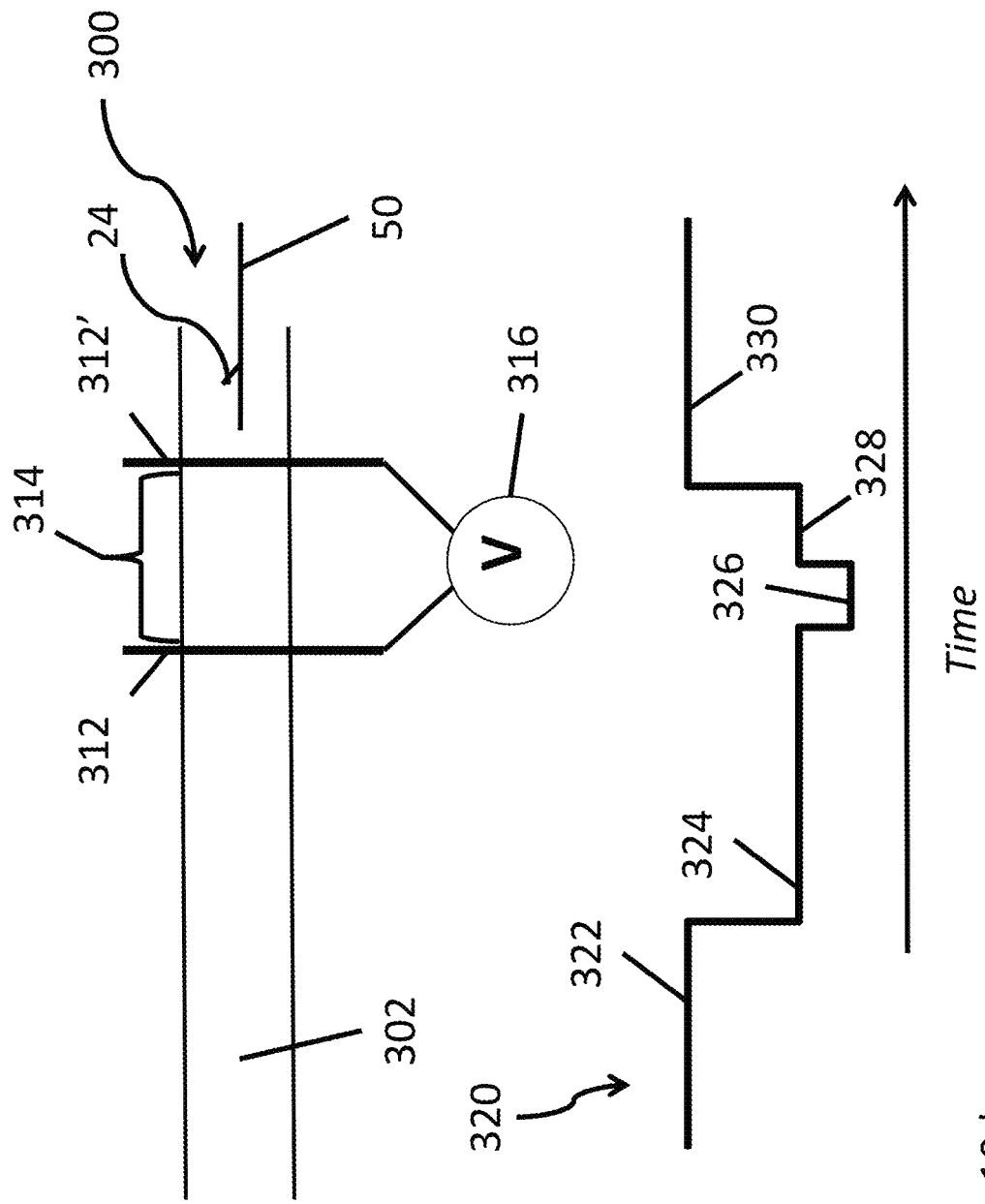
FIG. 10d is a schematic depiction of an electrical potential measurement as a DNA molecule having a flap exits a detection volume in the apparatus of FIG. 9.
Figure 11:
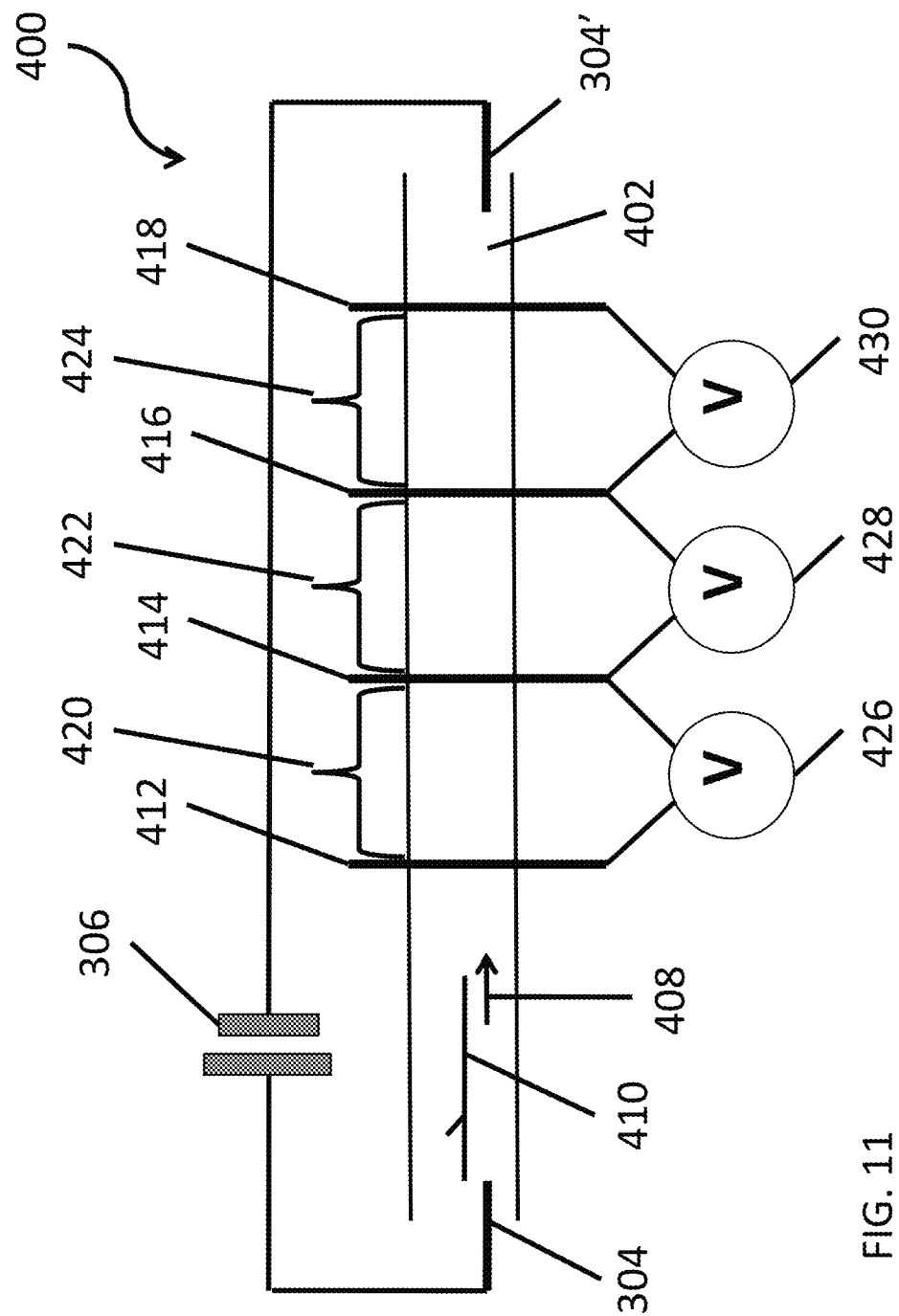
FIG. 11 is a schematic depiction of a nano-channel or micro-channel apparatus having multiple detection volumes.

In another embodiment, an electrical property such as electrical potential or current is measured during translocation of a DNA strand through a nano-channel or micro-channel as shown in FIGS. 9 through 11. One embodiment of a fluidic channel apparatus is shown schematically in FIG. 9. In FIG. 9, the apparatus 300 comprises a fluidic micro-channel or nano-channel 302. The fluidic channel may be a micro-channel having a width selected from a range of about 1 μm to about 25 μm or a nano-channel having a width selected from a range of about 10 nm to about 1 μm. In the case of a micro-channel, the depth may be selected from a range of about 200 nm to about 5 μm, whereas in the case of a nano-channel, the depth may be selected from a range of about 10 nm to about 1 μm. In either case, the channel may have a length selected from a range of about 1 μm to about 10 cm.

A first pair of electromotive electrodes 304, 304' is connected to a voltage source 306 and positioned in a spaced apart relationship in the channel. When a potential is applied to the electromotive electrodes, these electrodes provide an electrical current along the channel and may be used to provide or enhance a driving force 308 to a target analyte 50 in the channel. Other driving forces such as pressure or chemical gradients are contemplated as well. A second pair of electrodes 312, 312', i.e., detector electrodes, is positioned preferably substantially perpendicular to the channel in a spaced apart relationship to define a detection volume 314. The second pair of detector electrodes 312, 312' is connected to a detector 316, such as a voltmeter, which monitors an electrical property in the detection volume 314. In an embodiment where the detector 316 is a voltmeter, an electrical potential between the pair of detector electrodes 312, 312', is measured across the detection volume 314.

The operation of the device is depicted schematically in FIGS. 10a-10d in which changes in an electrical property across a fluidic channel are monitored, as the target analyte is translocated therethrough, with the changes in the electrical property being indicative of double-stranded regions of the target analyte and of the flap regions. In FIGS. 10a-10d, the first pair of electromotive electrodes 304, 304' and the current source 306 have been omitted for clarity. In FIG. 10a, the fluidic channel 302 contains a target analyte 50 traveling therethrough. An electrical property, in this case electrical potential, is measured and recorded across the detection volume 314 by the detector electrodes 312, 312' and the detector 316. The target analyte 50 is a DNA fragment upon which has been formed a flap 24 using the methods described previously. The DNA fragment and/or the flap may be coated with a binding moiety, such as the protein RecA, to enhance detection.

Prior to the entry of the target analyte 50 into the detection volume 314, a substantially constant voltage 322 is measured across the detection volume. This voltage is shown in the waveform 320 of FIG. 10a. As the target analyte 50 enters the detection volume 314, it causes an interruption or decrease in the electrical property measured in the detection volume. This interruption or decrease causes a first trough 324 to be exhibited in the waveform 320.

FIG. 10b shows the device and waveform 320 once the portion of the target analyte 50 including the flap 24 has entered the detection volume 314. Entry of the flap 24 into the detection volume 314 causes a further interruption or decrease in the electrical property measured in the detection volume. This further interruption or decrease causes a second trough 326 to be exhibited in the waveform 320.

In FIG. 10c, the portion of the target analyte 50 containing the flap 24 has exited the detection volume 314; however, a distal portion of the target analyte 50 may still be present in the detection volume. As a result, the waveform 320 has returned to a level 328 approximating that detected when the initial portion of the analyte first entered the detection volume.

Finally, as shown in FIG. 10d, the target analyte 50 has fully exited the detection volume 314. As a result, the waveform 320 has returned to a level 330 approximating that detected prior to initial entry of the analyte into the detection volume. Analysis of the waveform 320 permits differentiation between double-stranded DNA and flap regions of the target analyte based, at least in part, on the detected changes in the electrical property, to thereby determine nick locations and map at least a portion of the double-stranded DNA template.

Another embodiment of a fluidic channel apparatus is shown in FIG. 11. In FIG. 11, the apparatus 400 comprises a fluidic micro-channel or nano-channel 402. As before, the fluidic channel may be a micro-channel having a width selected from a range of about 1 μm to about 25 μm or a nano-channel having a width selected from a range of about 10 nm to about 1 μm. In the case of a micro-channel, the depth may be selected from a range of about 200 nm to about 5 μm, whereas in the case of a nano-channel, the depth may be selected from a range of about 10 nm to about 1 μm. In either case, the channel may have a length selected from a range of about 1 μm to about 10 cm.

A first pair of electromotive electrodes 304, 304' is connected to a voltage source 306 and positioned in a spaced apart relationship in the channel. When a potential is applied to the electromotive electrodes, these electrodes provide an electrical current along the channel and may be used to provide or enhance a driving force 408 to an analyte 410 in the channel. Other driving forces such as pressure or chemical gradients are contemplated as well. Multiple detector electrodes 412, 414, 416, 418, are positioned preferably perpendicular to the channel in a spaced apart relationship to define a plurality of detection volumes between adjacent detector electrodes. Thus, as seen in FIG. 11, detector electrodes 412 and 414 define detection volume 420, detector electrodes 414 and 416 define detection volume 422, and detector electrodes 416 and 418 define detection volume 424. The detector electrodes are each connected to detectors 426, 428, 430 such as voltmeters, which monitor an electrical property in each detection volume. In the embodiment where the detectors are voltmeters, a drop in electrical potential is measured across each detection volume. Operation of the apparatus is similar to that of the system of FIG. 10, with the exception that additional waveforms are generated due to the presence of additional detection volumes. The additional waveforms may be combined to further improve the quality of the data being generated by the device.

It should be understood that number of detector electrodes and detection volumes is not intended to limited to those depicted in FIG. 11. Rather, any number of detection volumes may be included along the length of the fluidic channel. Further, the detector electrodes and detection volumes need not be evenly spaced, evenly sized or directly adjacent to one another. Various detection volume sizes, spacing and configurations are contemplated.

Both the nanopore apparatus and the fluidic channel apparatus allow detection of an analyte as well as detection of a flap formed on that analyte. Furthermore, relative or absolute positional information of the flap may be obtained. Since, when using a known nicking endonuclease a specific recognition sequence is known, determination of the location of the flap allows determination of the location of the known recognition sequence. This in turn, allows the biomolecule to be mapped. The repeated use of different nicking endonucleases allows greater complexity, i.e., multiple recognition sequences, to be combined and mapped.

EQUIVALENTS

Several of the illustrated examples show DNA templates having a single nick formed thereon, with a single flap being formed thereafter. Embodiments of the present invention are not intended to be limited as such; rather, it is contemplated that a nicking endonuclease may form a plurality of nicks at sequence specific locations on a first DNA strand.

Those skilled in the art will readily appreciate that all parameters listed herein are meant to be exemplary and actual parameters depend upon the specific application for which the methods and materials of embodiments of the present invention are used. It is, therefore, to be understood that the foregoing embodiments are presented by way of example only and that, within the scope of the appended claims and equivalents thereto, the invention may be practiced otherwise than as specifically described. Thus, numerous variations and modifications will be apparent to those skilled in the art. All such variations and modifications are intended to be within the scope of the present invention as defined in the appended claims.

What is claimed is:

1. A method for preparing and analyzing a target analyte, the method comprising:
   a. providing a double-stranded DNA template having a first and a second DNA strand, each DNA strand having a 5' end and a 3' end,
   b. contacting the double-stranded DNA template with a nicking endonuclease to form a nick at a sequence-specific nicking location on the first DNA strand,
   c. conducting a base extension reaction on the first DNA strand along a corresponding region of the second DNA strand, said reaction starting at the nick and progressing toward the 3' end of the first DNA strand to thereby form a single-stranded flap on the double-stranded DNA template adjacent to the sequence-specific nicking location, to thereby prepare the target analyte, and
   d. monitoring changes in an electrical property across a nanopore as the target analyte is translocated therethrough, the changes in the electrical property being indicative of double-stranded regions of the target analyte and of the single-stranded flap regions.

2. The method of claim 1, wherein the nicking endonuclease comprises one or more endonucleases selected from the group consisting of Nb.BbvCI, Nb.BsmI, NbBsrDI, Nb.BtsI, Nt.AlwI, Nt.BbvCI, Nt.BsmAI, Nt.BspQI, Nt.BstNBI, and Nt.CviPII.

3. The method of claim 1, wherein the base extension reaction comprises contacting the first DNA strand with a polymerase, one or more nucleotides, a ligase, or any combination thereof.

4. The method of claim 1, further comprising coating the double-stranded DNA template with a binding moiety.

5. The method of claim 4, wherein the binding moiety comprises a protein.

6. The method of claim 5, wherein said protein includes one or more proteins selected from the group consisting of RecA, T4 gene 32 protein, f1 geneV protein, human replication protein A, Pf3 single-stranded binding protein, adenovirus DNA binding protein, and *E. coli* single-stranded binding protein.

7. The method of claim 1, further comprising:
   differentiating between double-stranded and single-stranded flap regions of the target analyte based, at least in part, on the detected changes in the electrical property, to thereby determine nick locations and map at least a portion of the double-stranded DNA template.

8. The method of claim 1, wherein preparing the target analyte further comprises conducting a second base extension reaction on the flap region to form a double-stranded flap.

9. The method of claim 8, further comprising adding a single-stranded extension to the double-stranded flap, and hybridizing one or more probes to the single-stranded extension.

10. The method of claim 9, wherein the single-stranded extension added to the double-stranded flap is a single-stranded polyT extension.

11. The method of claim 10, wherein the probes comprise polyA oligomers.

12. The method of claim 9, wherein the single-stranded extension added to the double-stranded flap is a single-stranded polyA extension.

13. The method of claim 12, wherein the probes comprise polyT oligomers.

14. The method of claim 9, wherein the probes are tagged.

15. The method of claim 14, wherein the probes are tagged using gold particles.

16. The method of claim 9, wherein the single-stranded extension is added to the double-stranded flap using a terminal transferase.

17. The method of claim 9, wherein the single-stranded extension is at least 100 bases in length.

18. A method for preparing and analyzing a target analyte, the method comprising:
   a. providing a double-stranded DNA template having a first and a second DNA strand, each DNA strand having a 5' end and a 3' end,
   b. contacting the double-stranded DNA template with a nicking endonuclease to form a nick at a sequence-specific nicking location on the first DNA strand,
   c. conducting a base extension reaction on the first DNA strand along a corresponding region of the second DNA strand, said reaction starting at the nick and progressing toward the 3' end of the first DNA strand to thereby form a single-stranded flap on the double-stranded DNA template adjacent to the sequence-specific nicking location, to thereby prepare the target analyte, and
   d. monitoring changes in an electrical property across a fluidic channel as the target analyte is translocated therethrough, the changes in the electrical property being indicative of double-stranded regions of the target analyte and of the single-stranded flap regions.

19. The method of claim 18, wherein the fluidic channel comprises a micro-channel or a nano-channel.

20. The method of claim 18, further comprising:
   differentiating between double-stranded and single-stranded flap regions of the target analyte based, at least in part, on the detected changes in the electrical property, to thereby determine nick locations and map at least a portion of the double-stranded DNA template.

21. The method of claim 18, wherein the nicking endonuclease comprises one or more endonucleases selected from the group consisting of Nb.BbvCI, Nb.BsmI, NbBsrDI, Nb.BtsI, Nt.AlwI, Nt.BbvCI, Nt.BsmAI, Nt.BspQI, Nt.BstNBI, and Nt.CviPII.

22. The method of claim 18, wherein the base extension reaction comprises contacting the first DNA strand with a polymerase, one or more nucleotides, a ligase, or any combination thereof.

23. The method of claim 18, further comprising coating the double-stranded DNA template with a binding moiety.

24. The method of claim 23, wherein the binding moiety comprises a protein.

25. The method of claim 24, wherein said protein includes one or more proteins selected from the group consisting of RecA, T4 gene 32 protein, f1 geneV protein, human replication protein A, Pf3 single-stranded binding protein, adenovirus DNA binding protein, and *E. coli* single-stranded binding protein.

26. The method of claim 18, wherein preparing the target analyte further comprises conducting a second base extension reaction on the flap region to form a double-stranded flap.

27. The method of claim 26, further comprising adding a single-stranded extension to the double-stranded flap, and hybridizing one or more probes to the single-stranded extension.

28. The method of claim 27, wherein the single-stranded extension added to the double-stranded flap is a single-stranded polyT extension.

29. The method of claim 28, wherein the probes comprise polyA oligomers.

30. The method of claim 27, wherein the single-stranded extension added to the double-stranded flap is a single-stranded polyA extension.

31. The method of claim 30, wherein the probes comprise polyT oligomers.

32. The method of claim 27, wherein the probes are tagged.

33. The method of claim 32, wherein the probes are tagged using gold particles.

34. The method of claim 27, wherein the single-stranded extension is added to the double-stranded flap using a terminal transferase.

35. The method of claim 27, wherein the single-stranded extension is at least 100 bases in length.

36. A method for preparing a target analyte, the method comprising:
   a. providing a double-stranded DNA template having first and second DNA strands, each strand having a 5' end and a 3' end,
   b. contacting the template with a nicking endonuclease to form nicks at sequence-specific locations on the first DNA strand,
   c. conducting a first base extension reaction on the first DNA strand along the corresponding region of the second DNA strand, said reaction starting at each nick and progressing toward the 3' end of the first DNA strand to thereby form single-stranded flap regions on the double-stranded DNA template adjacent to the sequence-specific nicking locations,
   d. conducting a second base extension reaction on at least one single-stranded flap region to form at least one double-stranded flap,
   e. adding a single-stranded extension to the double-stranded flap, and
   f. hybridizing one or more probes to the single-stranded extension, to thereby prepare the target analyte, wherein the probes are tagged using gold particles.

\* \* \* \* \*